(12) United States Patent
Wang et al.

(10) Patent No.: US 10,307,407 B2
(45) Date of Patent: Jun. 4, 2019

(54) 9H-PYRIMIDO [4,5-B] INDOLES AS BET BROMODOMAIN INHIBITORS

(71) Applicant: THE REGENTS OF THE UNIVERSITY OF MICHIGAN, Ann Arbor, MI (US)

(72) Inventors: Shaomeng Wang, Superior Township, MI (US); Yujun Zhao, Ann Arbor, MI (US); Bing Zhou, Ann Arbor, MI (US); Angelo Aguilar, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/553,593

(22) PCT Filed: Feb. 26, 2016

(86) PCT No.: PCT/US2016/019674
§ 371 (c)(1),
(2) Date: Aug. 25, 2017

(87) PCT Pub. No.: WO2016/138332
PCT Pub. Date: Sep. 1, 2016

(65) Prior Publication Data
US 2018/0036294 A1    Feb. 8, 2018

Related U.S. Application Data

(60) Provisional application No. 62/121,637, filed on Feb. 27, 2015.

(51) Int. Cl.
| | |
|---|---|
| C07D 487/04 | (2006.01) |
| C07D 487/14 | (2006.01) |
| A61K 31/437 | (2006.01) |
| A61K 31/519 | (2006.01) |
| C07D 231/38 | (2006.01) |
| C07D 261/06 | (2006.01) |
| C07D 471/04 | (2006.01) |

(52) U.S. Cl.
CPC .......... *A61K 31/437* (2013.01); *A61K 31/519* (2013.01); *C07D 231/38* (2013.01); *C07D 261/06* (2013.01); *C07D 471/04* (2013.01); *C07D 487/04* (2013.01); *C07D 487/14* (2013.01)

(58) Field of Classification Search
CPC ............................. C07D 471/04; C07D 487/04
See application file for complete search history.

(56) References Cited

U.S. PATENT DOCUMENTS

| | | | |
|---|---|---|---|
| 4,835,160 A * | 5/1989 | Bisagni ................ | C07D 471/04 514/292 |
| 8,044,042 B2 | 10/2011 | Adachi et al. | |
| 8,114,995 B2 | 2/2012 | Hansen et al. | |
| 8,476,260 B2 | 7/2013 | Miyoshi et al. | |
| 8,557,984 B2 | 10/2013 | Bouillot et al. | |
| 8,580,957 B2 | 11/2013 | Demont et al. | |
| 2009/0099165 A1 | 4/2009 | Hurley et al. | |
| 2009/0143399 A1 | 6/2009 | Hurley et al. | |
| 2010/0286127 A1 | 11/2010 | Miyoshi et al. | |
| 2012/0059002 A1 | 3/2012 | Hansen et al. | |

(Continued)

FOREIGN PATENT DOCUMENTS

| | | |
|---|---|---|
| WO | WO-1998/011111 A1 | 3/1998 |
| WO | WO-2006/129623 A1 | 12/2006 |

(Continued)

OTHER PUBLICATIONS

Written Opinion of the International Search Authority for Application No. PCT/US2016/019674, dated Aug. 29, 2017.
Caira et al., Preparation and crystal characterization of a polymorph, a monohydrate, and an ethyl acetate solvate of the antifungal fluconazole, J. Pharm. Sci., 93(3):601-11 (2004).
Delmore et al., BET bromodomain inhibition as a therapeutic strategy to target c-Myc, Cell, 146(6):904-17 (2011).
International Search Report and Written Opinion, International Application No. PCT/US2016/019674, dated Jun. 17, 2016.
Ma et al., Asymmetric dipolar cycloaddition reactions: a practical, convergent synthesis of chiral pyrrolidines, Tetrahedron: Asymmetry, 80(6):883-7 (1997).

(Continued)

*Primary Examiner* — Shawquia Jackson
(74) *Attorney, Agent, or Firm* — Marshall, Gerstein & Borun LLP

(57) ABSTRACT

The present disclosure provides substituted 9H-pyrimido [4,5-b] indoles and 5H-pyrido [4,3-b] indoles and related analogs represented by Formula I and the pharmaceutically acceptable salts, hydrates, and solvates thereof, wherein $R^{1a}$, W, $B^1$, $B^2$, G, $X^1$, $Y^1$, $Y^2$, and $Y^3$ are as defined as set forth in the specification. The present disclosure is also directed to the use of compounds of Formula I to treat a condition or disorder responsive to inhibition of BET bromodomains such as cancer. The present disclosure is also directed to the use of compound of Formula I as synthetic intermediates.

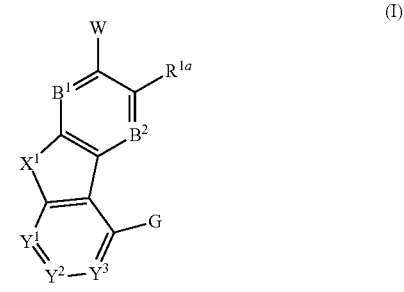

(I)

6 Claims, No Drawings

(56) References Cited

U.S. PATENT DOCUMENTS

| | | |
|---|---|---|
| 2012/0157428 A1 | 6/2012 | Albrecht et al. |
| 2012/0202799 A1 | 8/2012 | Crowe et al. |
| 2012/0208800 A1 | 8/2012 | Chung et al. |
| 2012/0252781 A1 | 10/2012 | Bailey et al. |
| 2013/0079335 A1 | 3/2013 | Bailey |
| 2013/0184264 A1 | 7/2013 | Bradner et al. |
| 2013/0252331 A1 | 9/2013 | Bradner et al. |
| 2013/0281399 A1 | 10/2013 | McLure et al. |
| 2013/0281450 A1 | 10/2013 | Pratt et al. |
| 2013/0331382 A1 | 12/2013 | Hubbard et al. |
| 2014/0005169 A1 | 1/2014 | Albrecht et al. |
| 2014/0011862 A1 | 1/2014 | Bradner et al. |

FOREIGN PATENT DOCUMENTS

| | | |
|---|---|---|
| WO | WO-2008/092231 A1 | 8/2008 |
| WO | WO-2009/084693 A1 | 7/2009 |
| WO | WO-2009/158404 A1 | 12/2009 |
| WO | WO-2010/123975 A1 | 10/2010 |
| WO | WO-2011/054843 A1 | 5/2011 |
| WO | WO-2011/054844 A1 | 5/2011 |
| WO | WO-2011/054845 A1 | 5/2011 |
| WO | WO-2011/054846 A1 | 5/2011 |
| WO | WO-2011/054848 A1 | 5/2011 |
| WO | WO-2011/054864 A1 | 5/2011 |
| WO | WO-2011/143651 A1 | 11/2011 |
| WO | WO-2011/143660 A2 | 11/2011 |
| WO | WO-2011/143669 A2 | 11/2011 |
| WO | WO-2011/161031 A1 | 12/2011 |
| WO | WO-2012/075383 A2 | 6/2012 |
| WO | WO-2012/075456 A1 | 6/2012 |
| WO | WO-2012/116170 A1 | 8/2012 |
| WO | WO-2012/151512 A2 | 11/2012 |
| WO | WO-2012/174487 A2 | 12/2012 |
| WO | WO-2013/024104 A1 | 2/2013 |
| WO | WO-2013/027168 A1 | 2/2013 |
| WO | WO-2013/030150 A1 | 3/2013 |
| WO | WO-2013/033268 A2 | 3/2013 |
| WO | WO-2013/097601 A1 | 7/2013 |
| WO | WO-2015/131005 A1 | 9/2015 |

OTHER PUBLICATIONS

Seal et al., Identification of a novel series of BET family bromodomain inhibitors: binding mode and profile of I-BET151 (GSK1210151A), Bioorg. Med. Chem. Lett., 22(8):2968-72 (2012).

Van Tonder et al., Preparation and physicochemical characterization of 5 niclosamide solvates and 1 hemisolvate, AAPS PharmSciTech, 591):E12 (2004).

* cited by examiner

9H-PYRIMIDO [4,5-B] INDOLES AS BET BROMODOMAIN INHIBITORS

CROSS-REFERENCE TO RELATED APPLICATION

The priority benefit of U.S. Provisional Patent Application No. 62/121,637, filed Feb. 27, 2015, is claimed, and the entire contents thereof are expressly incorporated herein by reference.

BACKGROUND OF THE INVENTION

Field of the Invention

The present disclosure provides BET bromodomain inhibitors and therapeutic methods of treating conditions and diseases wherein inhibition of one or more BET bromodomains provides a benefit.

Background Art

The genomes of eukaryotic organisms are highly organized within the nucleus of the cell. The long strands of duplex DNA are wrapped around an octamer of histone proteins (usually comprising two copies of histones H2A, H2B, H3, and H4) to form a nucleosome, which then is further compressed to form a highly condensed chromatin structure. A range of different condensation states are possible, and the tightness of this structure varies during the cell cycle. The chromatin structure plays a critical role in regulating gene transcription, which cannot occur efficiently from highly condensed chromatin. The chromatin structure is controlled by a series of post translational modifications to histone proteins, notably histones H3 and H4. These modifications include acetylation, methylation, phosphorylation, ubiquitinylation, and SUMOylation.

Histone acetylation usually is associated with the activation of gene transcription, as the modification loosens the interaction of the DNA and the histone octamer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly, but not exclusively, in the context of histones. There is a family of about 50 proteins known to contain bromodomains, which have a range of functions within the cell.

The BET family of bromodomain-containing proteins ("BET bromodomains") includes four proteins, i.e., BRD2, BRD3, BRD4, and BRD-t, which contain tandem bromodomains capable of binding to two acetylated lysine residues in close proximity, thereby increasing the specificity of the interaction. BRD2 and BRD3 associate with histones along actively transcribed genes and may be involved in facilitating transcriptional elongation, while BRD4 may be involved in the recruitment of the pTEF-β complex to inducible genes, resulting in phosphorylation of RNA polymerase and increased transcriptional output. BRD4 or BRD3 also may fuse with NUT (nuclear protein in testis) forming novel fusion oncogenes, BRD4-NUT or BRD3-NUT, in a highly malignant form of epithelial neoplasia. Data suggests that BRD-NUT fusion proteins contribute to carcinogenesis. BRD-t is uniquely expressed in the testes and ovary. All family members have been reported to have some function in controlling or executing aspects of the cell cycle, and have been shown to remain in complex with chromosomes during cell division, which suggests a role in the maintenance of epigenetic memory. In addition, some viruses make use of these proteins to tether their genomes to the host cell chromatin as part of the process of viral replication.

A discussion of BET proteins can be found in WO 2012/075456, WO 2012/075383, and WO 2011/054864. A discussion of BET bromodomain inhibitors, e.g., I-BET-151 and I-BET-762, can be found in Delmore et al., *Cell* 146: 904-917 (2011) and Seal et al., *Bioorg. Med. Chem. Lett.* 22:2968-2972 (2012). Small molecule inhibitors of BET bromodomains have therapeutic potential for the treatment of many diseases and conditions in which BET bromodomains have a role, including cancer. BET bromodomain inhibitors are disclosed in the following U.S. patents: U.S. Pat. Nos. 8,044,042, 8,476,260, 8,114,995, 8,557,984, and 8,580,957; the following U.S. patent application publications: US 20120059002, US 20120208800, US 2012202799, US 2012252781, US 20130252331, US 20140011862, US 20130184264, US 2013079335, US 20140011862, US 20140005169, US 20130331382, US 20130281450, US 20130281399, US 20120157428, and US 20100286127; and the following international applications: WO 1998011111, WO 2006129623, WO 2008092231, WO 2009084693, WO 2009158404, WO 2010123975, WO 2011054843, WO 2011054844, WO 2011054845, WO 2011054846, WO 2011054848, WO 2011143651, WO 2011143660, WO 2011143669, WO 2011161031, WO 2012075383, WO 2012116170, WO 2012151512, WO 2012174487, WO 2013024104, WO 2013027168, WO 2013030150, WO 2013033268, and WO 2013097601.

Despite research directed to BET bromodomains and BET bromodomain inhibitors, the design of potent, non-peptide inhibitors of BET bromodomains remains a significant challenge in modern drug discovery. Accordingly, a need still exists in the art for BET bromodomain inhibitors having physical and pharmacological properties that permit use of the inhibitors in therapeutic applications, especially in humans. The present disclosure provides compounds that bind to BET bromodomains and inhibit BET bromodomain activity and synthetic intermediates that that can be used to prepare compounds that bind to BET bromodomains and inhibit BET bromodomain activity.

BRIEF SUMMARY OF THE INVENTION

In one aspect, the present disclosure provides 9H-pyrimido[4,5-b]indoles, 5H-pyrido[4,3-b]indoles, and related analogs represented by any one of Formulae I-VI, below, and the pharmaceutically acceptable salts, hydrates, and solvates thereof, collectively referred to herein as "Compounds of the Disclosure." Compounds of the Disclosure are inhibitors of BET bromodomains that bind to BET bromodomains and function as antagonists of BET bromodomains and/or synthetic intermediates that can be used to prepare inhibitors of BET bromodomains. Compounds of the Disclosure that inhibit BET bromodomains are useful in treating diseases or conditions wherein inhibition of BET bromodomains, e.g., BRD2, BRD3, BRD4, BRD-t, or an isoform or mutant thereof, provides a benefit.

In another aspect, the present disclosure provides methods of treating a condition or disease by administering a therapeutically effective amount of a Compound of the Disclosure to an individual, e.g., a human, in need thereof. The disease or condition of interest is treatable by inhibition of BET bromodomains, for example, a cancer, a chronic autoimmune disorder, an inflammatory condition, a proliferative disorder, sepsis, or a viral infection. Also provided are methods of preventing the proliferation of unwanted proliferating cells, such as cancer, in a subject comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis in those cells.

In another aspect, the present disclosure provides a method of inhibiting BET bromodomains in an individual, comprising administering to the individual an effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating diseases or conditions wherein inhibition of BET bromodomains provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure, e.g., compounds having any one of Formulae VII, X, XII, XIV, XVI, and XVIII.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Compounds of the Disclosure are inhibitors of BET bromodomain proteins and/or synthetic intermediates used to prepare inhibitors of BET bromodomain proteins.

In one embodiment, Compounds of the Disclosure are compounds represented by Formula I:

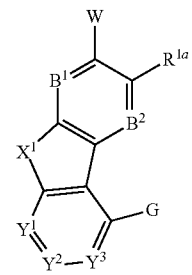

and the pharmaceutically acceptable salts, hydrates, and solvates thereof, wherein:

$B^1$ is —N═ or —C($R^{1b}$)—;

$B^2$ is —N═ or —C($R^{1c}$)—;

$Y^1$ is selected from the group consisting of —C($R^{2a}$)═ and —N═;

$Y^2$ is selected from the group consisting of —C($R^{2b}$)═ and —N═;

$Y^3$ is selected from the group consisting of —C($R^{2c}$)═ and —N═;

G is selected from the group consisting of halo, hydroxy, cyano, optionally substituted cycloalkyl, optionally substituted heterocyclo, optionally substituted aryl, optionally substituted heteroaryl, aralkyl, (heteroaryl)alkyl, —OS(═O)$_2$CF$_3$, and —Z—$R^3$ $R^{1a}$, $R^{1b}$, and $R^{1c}$ are each independently selected from the group consisting of hydrogen, hydroxy, alkyl, haloalkyl, alkoxy, alkylthio, amino, and fluoro;

$R^{2a}$ and $R^{2c}$ are independently selected from the group consisting of hydrogen, halo, alkyl, and carboxamido;

$R^{2b}$ is selected from the group consisting of hydrogen, amino, alkyl, hydroxyalkyl, alkoxyalkyl, heteroalkyl, (heterocyclo)alkyl, (amino)alkyl, optionally substituted cycloalkyl, optionally substituted heterocyclo, and carboxamido;

$R^3$ is selected from the group consisting of optionally substituted cycloalkyl, optionally substituted aryl, optionally substituted heteroaryl, and optionally substituted heterocyclo;

W is selected from the group consisting of A and L;

A is optionally substituted 5-membered heteroaryl;

L is a leaving group, e.g., Cl, I, Br, or OSO$_2$R$^6$, wherein $R^6$ is selected from the group consisting of alkyl, haloalkyl, and optionally substituted aryl;

$X^1$ is selected from the group consisting of —O—, —S—, and —N($R^{5a1}$)—;

Z is selected from the group consisting of —O—, —S—, —S$_2$—, and —N($R^{5b1}$)—;

$R^{5a1}$ is selected from the group consisting of hydrogen and alkyl; and $R^{5b1}$ is selected from the group consisting of hydrogen and alkyl, with the provisos that:

1) A is not 1,3-dimethyl-1H-pyrazol-4-yl, or:

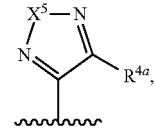

-continued

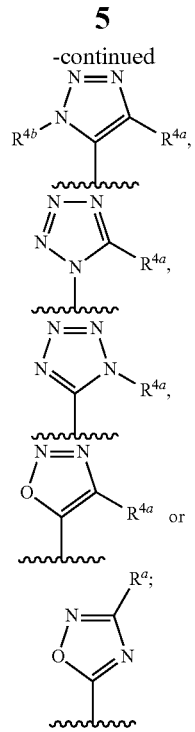

wherein:

$R^{4a}$ and $R^{4b}$ are each independently selected from the group consisting of hydrogen, halo, haloalkyl, and alkyl; and $X^5$ is selected from the group consisting of —O— and —S—; and 2) when $R^3$ is 3-cyclopropyl-1-methyl-1H-pyrazol-5-yl, then L is not Br.

In another embodiment, Compounds of the Disclosure are compounds represented by Formula II:

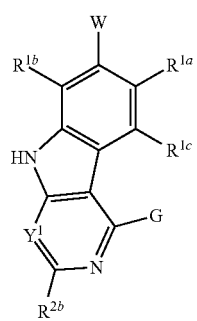

II and the pharmaceutically acceptable salts, hydrates, and solvates thereof, wherein $R^{1a}$, $R^{1b}$, $R^{1c}$, $R^{2b}$, $Y^1$, G, and W are as defined in connection with Formula I, with the provisos that:

1) A is not 1,3-dimethyl-1H-pyrazol-4-yl, or:

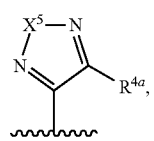

-continued

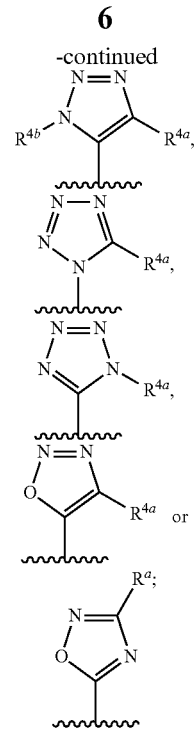

wherein:

$R^{4a}$ and $R^{4b}$ are each independently selected from the group consisting of hydrogen, halo, haloalkyl, and alkyl; and $X^5$ is selected from the group consisting of —O— and —S—; and 2) when $R^3$ is 3-cyclopropyl-1-methyl-1H-pyrazol-5-yl, then L is not Br.

In another embodiment, Compounds of the Disclosure are compounds represented by Formula II, and the pharmaceutically acceptable salts, hydrates, and solvates thereof, wherein:

G is selected from the group consisting of halo, hydroxy, cyano, optionally substituted cycloalkyl, optionally substituted heterocyclo, optionally substituted aryl, optionally substituted heteroaryl, aralkyl, (heteroaryl)alkyl, and —OS($=$O)$_2$CF$_3$.

In another embodiment, Compounds of the Disclosure are compounds represented by Formula III:

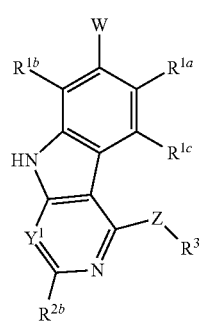

III and the pharmaceutically acceptable salts, hydrates, and solvates thereof, wherein $R^{1a}$, $R^{1b}$, $R^{1c}$, $R^{2b}$, $R^3$, $Y^1$, Z, and W are as defined in connection with Formula I, with the provisos that:
1) A is not 1,3-dimethyl-1H-pyrazol-4-yl, or:

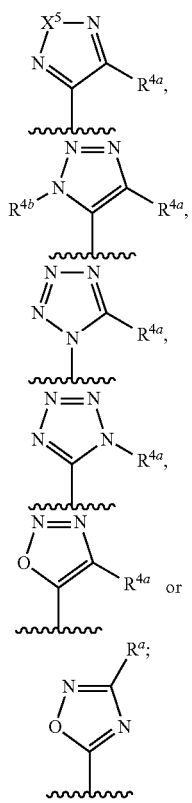

wherein:
$R^{4a}$ and $R^{4b}$ are each independently selected from the group consisting of hydrogen, halo, haloalkyl, and alkyl; and
$X^5$ is selected from the group consisting of —O— and —S—; and
2) when $R^3$ is 3-cyclopropyl-1-methyl-1H-pyrazol-5-yl, then L is not Br.

In another embodiment, Compounds of the Disclosure are compounds represented by Formula III, and the pharmaceutically acceptable salts, hydrates, and solvates thereof, wherein Z is selected from the group consisting of —O— and —N(H)—.

In another embodiment, Compounds of the Disclosure are compounds represented by Formula IV:

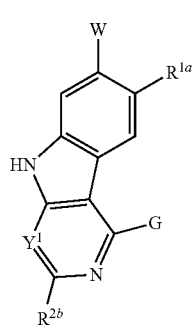

IV and the pharmaceutically acceptable salts, hydrates, and solvates thereof, wherein:

G is optionally substituted heteroaryl; and
$R^{1a}$, $R^{2b}$, $Y^1$, and W is as defined in connection with Formula I,
with the provisos that:
1) A is not 1,3-dimethyl-1H-pyrazol-4-yl, or:

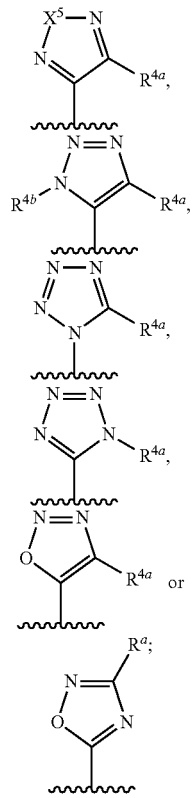

wherein:
$R^{4a}$ and $R^{4b}$ are each independently selected from the group consisting of hydrogen, halo, haloalkyl, and alkyl; and
$X^5$ is selected from the group consisting of —O— and —S—; and
2) when $R^3$ is 3-cyclopropyl-1-methyl-1H-pyrazol-5-yl, then L is not Br.

In another embodiment, Compounds of the Disclosure are compounds represented by Formula V:

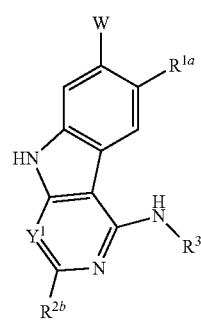

V and the pharmaceutically acceptable salts, hydrates, and solvates thereof, wherein:

R³ is optionally substituted heteroaryl; and

R¹ᵃ, R²ᵇ, Y¹, and W are as defined in connection with Formula I, with the provisos that:

1) A is not 1,3-dimethyl-1H-pyrazol-4-yl, or:

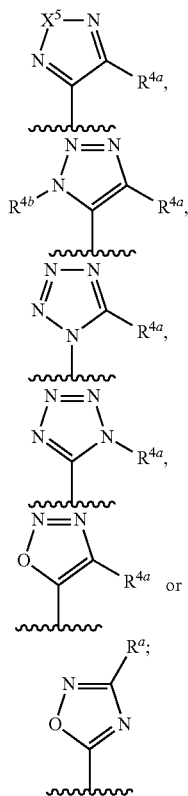

wherein:

R⁴ᵃ and R⁴ᵇ are each independently selected from the group consisting of hydrogen, halo, haloalkyl, and alkyl; and X⁵ is selected from the group consisting of —O— and —S—; and 2) when R³ is 3-cyclopropyl-1-methyl-1H-pyrazol-5-yl, then L is not Br.

In another embodiment, Compounds of the Disclosure are compounds represented by any one of Formulae I, II, or IV, and the pharmaceutically acceptable salts, hydrates, and solvates thereof, wherein G is optionally substituted 6-membered heteroaryl, e.g., an optionally substituted pyridyl, e.g., wherein the optional substituent is a $C_{1-6}$ alkyl.

In another embodiment, Compounds of the Disclosure are compounds represented by any one of Formulae I, III, or V, and the pharmaceutically acceptable salts, hydrates, and solvates thereof, wherein R³ is selected from the group consisting of:

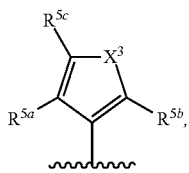 R3-1

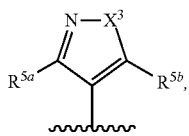 R3-2

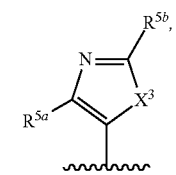 R3-3

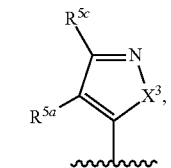 R3-4

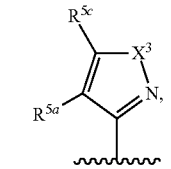 R3-5

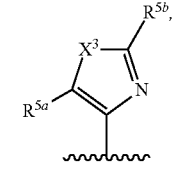 R3-6

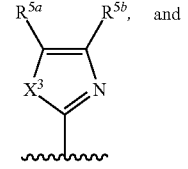 R3-7

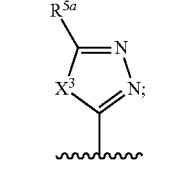 R3-8

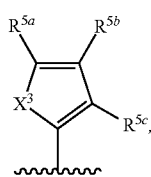 R3-9

$R^{5a}$, $R^{5b}$, and $R^{5c}$ are each independently selected from the group consisting of hydrogen, halo, cyano, alkylcarbonyl, alkoxycarbonyl, haloalkyl, optionally substituted alkyl, hydroxyalkyl, alkoxyalkyl, alkenyl, aralkyl, optionally substituted cycloalkyl, optionally substituted heterocyclo, optionally substituted aryl, optionally substituted heteroaryl, and carboxamido;

$X^3$ is selected from the group consisting of —O—, —S—, and —N($R^{5d}$)—;

$R^{5d}$ is selected from the group consisting of hydrogen, alkyl, haloalkyl, hydroxyalkyl, alkoxyalkyl, (amino)alkyl, aralkyl, optionally substituted cycloalkyl, optionally substituted heterocyclo, optionally substituted aryl, optionally substituted heteroaryl, carboxamido, (carboxamido)alkyl, and —C(=O)$R^{5e}$; and $R^{5e}$ is selected from the group consisting of alkyl and alkoxy.

In another embodiment, Compounds of the Disclosure are compounds represented by any one of Formulae I, III, or V, and the pharmaceutically acceptable salts, hydrates, and solvates thereof, wherein:

$R^3$ is optionally substituted heteroaryl selected from the group consisting of:

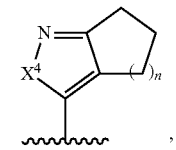
R3-10

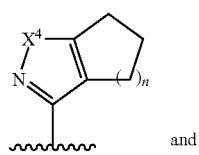
and
R3-11

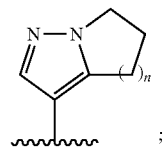
;
R3-12

$X^4$ is selected from the group consisting of —O—, —S—, and —N($R^{5f}$)—;

$R^{5f}$ is selected from the group consisting of hydrogen, alkyl, haloalkyl, hydroxyalkyl, aralkyl, optionally substituted cycloalkyl, optionally substituted aryl, optionally substituted heteroaryl, and carboxamido; and n is 1, 2, or 3. In another embodiment, $X^4$ is —N($R^{5f}$)— and n is 1 or 2.

In another embodiment, Compounds of the Disclosure are compounds represented by any one of Formulae I, III, or V, and the pharmaceutically acceptable salts, hydrates, and solvates thereof, wherein $R^3$ is R3-1.

In another embodiment, Compounds of the Disclosure are compounds represented by any one of Formulae I, III, or V, and the pharmaceutically acceptable salts, hydrates, and solvates thereof, wherein $R^3$ is R3-2.

In another embodiment, Compounds of the Disclosure are compounds represented by any one of Formulae I, III, or V, and the pharmaceutically acceptable salts, hydrates, and solvates thereof, wherein $R^3$ is R3-3.

In another embodiment, Compounds of the Disclosure are compounds represented by any one of Formulae I, III, or V, and the pharmaceutically acceptable salts, hydrates, and solvates thereof, wherein $R^3$ is R3-4.

In another embodiment, Compounds of the Disclosure are compounds represented by any one of Formulae I, III, or V, and the pharmaceutically acceptable salts, hydrates, and solvates thereof, wherein $R^3$ is R3-5.

In another embodiment, Compounds of the Disclosure are compounds represented by any one of Formulae I, III, or V, and the pharmaceutically acceptable salts, hydrates, and solvates thereof, wherein $R^3$ is R3-6.

In another embodiment, Compounds of the Disclosure are compounds represented by any one of Formulae I, III, or V, and the pharmaceutically acceptable salts, hydrates, and solvates thereof, wherein $R^3$ is R3-7.

In another embodiment, Compounds of the Disclosure are compounds represented by any one of Formulae I, III, or V and the pharmaceutically acceptable salts, hydrates, and solvates thereof, wherein $R^3$ is R3-8.

In another embodiment, Compounds of the Disclosure are compounds represented by any one of Formulae I, III, or V, and the pharmaceutically acceptable salts, hydrates, and solvates thereof, wherein $R^3$ is R3-9.

In another embodiment, Compounds of the Disclosure are compounds represented by any one of Formulae I, III, or V, and the pharmaceutically acceptable salts, hydrates, and solvates thereof, wherein $R^3$ is R3-10.

In another embodiment, Compounds of the Disclosure are compounds represented by any one of Formulae I, III, or V, and the pharmaceutically acceptable salts, hydrates, and solvates thereof, wherein $R^3$ is R3-11.

In another embodiment, Compounds of the Disclosure are compounds represented by any one of Formulae I, III, or V, and the pharmaceutically acceptable salts, hydrates, and solvates thereof, wherein $R^3$ is R3-12.

In another embodiment, Compounds of the Disclosure are compounds represented by any one of Formulae I, III, or V, and the pharmaceutically acceptable salts, hydrates, and solvates thereof, wherein $R^3$ is selected from the group consisting of:

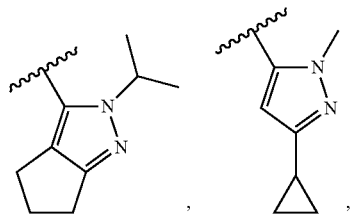
,

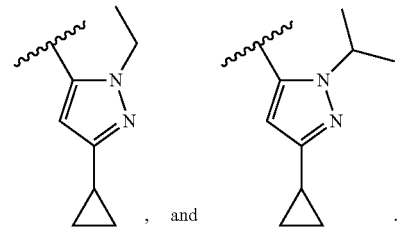
, and .

In another embodiment, Compounds of the Disclosure are compounds represented by Formula VI:

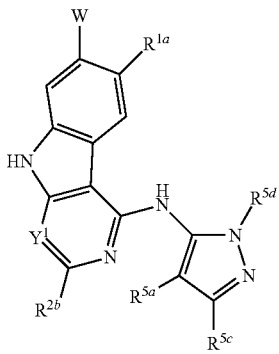

and the pharmaceutically acceptable salts, hydrates, and solvates thereof, wherein $R^{1a}$, $R^{2b}$, $R^{5a}$, $R^{5c}$, $R^{5d}$, $Y^1$, and W are as defined above in connection with Formula I, with the provisos that:
1) A is not 1,3-dimethyl-1H-pyrazol-4-yl, or:

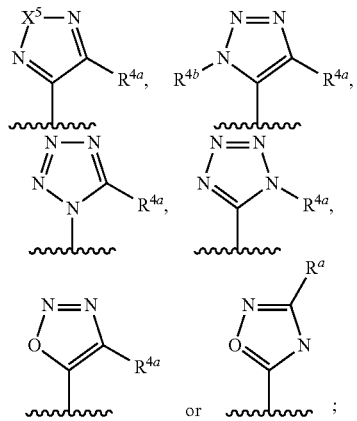

wherein:
$R^{4a}$ and $R^{4b}$ are each independently selected from the group consisting of hydrogen, halo, haloalkyl, and alkyl; and
$X^5$ is selected from the group consisting of —O— and —S—; and
2) when $R^3$ is 3-cyclopropyl-1-methyl-1H-pyrazol-5-yl, then L is not Br.

In another embodiment, Compounds of the Disclosure are compounds represented by Formula VI, and the pharmaceutically acceptable salts, hydrates, and solvates thereof, wherein $R^{5a}$, $R^{5c}$, and $R^{5d}$ are independently selected from the group consisting of hydrogen, $C_{1-6}$ alkyl, and $C_{3-6}$ cycloalkyl.

In another embodiment, Compounds of the Disclosure are compounds represented by any one of Formula I-VI, and the pharmaceutically acceptable salts, hydrates, and solvates thereof, wherein, $R^{1a}$ is alkoxy. In another embodiment, $R^{1a}$ is methoxy.

In another embodiment, Compounds of the Disclosure are compounds represented by any one of Formula I-VI, and the pharmaceutically acceptable salts, hydrates, and solvates thereof, wherein, $R^{2b}$ is selected from the group consisting of alkyl or alkoxyalkyl. In another embodiment, $R^{2b}$ is selected from the group consisting of —$CH_3$ and —$CH_2OCH_3$.

In another embodiment, Compounds of the Disclosure are compounds represented by any one of Formula I-VI, and the pharmaceutically acceptable salts, hydrates, and solvates thereof, wherein, $Y^1$ is —N=.

In another embodiment, Compounds of the Disclosure are compounds represented by any one of Formula I-VI, and the pharmaceutically acceptable salts, hydrates, and solvates thereof, wherein, $Y^1$ is —CH=.

In another embodiment, Compounds of the Disclosure are compounds represented by any one of Formulae I-VI, and the pharmaceutically acceptable salts, hydrates, and solvates thereof, wherein W is L. See the compounds represented by Formulae VII, X, XII, XIV, XVI, and XVIII, below. In another embodiment, L is selected from the group consisting of Cl, I, Br, and $OSO_2R^6$, wherein $R^6$ is selected from the group consisting of alkyl, haloalkyl, and optionally substituted aryl. In another embodiment, L is Br. In another embodiment, L is —$OSO_2CF_3$.

In another embodiment, Compounds of the Disclosure are compounds represented by any one of Formulae I-VI, and the pharmaceutically acceptable salts, hydrates, and solvates thereof, wherein W is A. See the compounds represented by Formulae VIII, XI, XIII, XV, XVII, and XIX, below.

In another embodiment, Compounds of the Disclosure are compounds represented by any one of Formulae I-VI, and the pharmaceutically acceptable salts, hydrates, and solvates thereof, wherein W is A. In another embodiment, A is selected from the group consisting of:

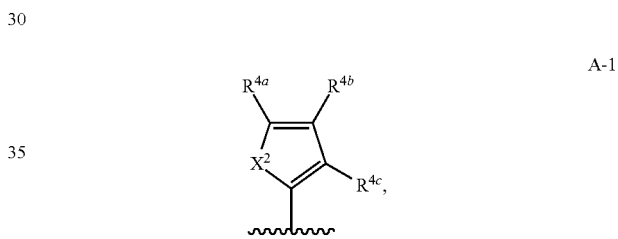

A-1

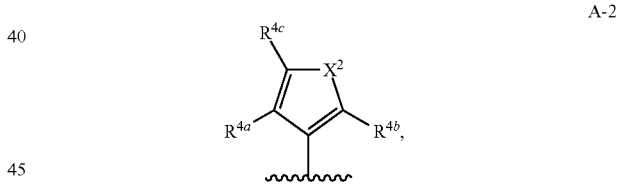

A-2

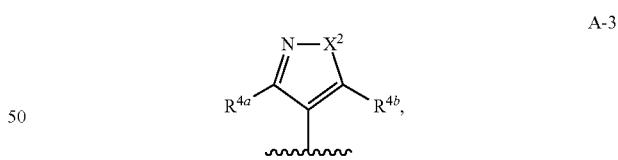

A-3

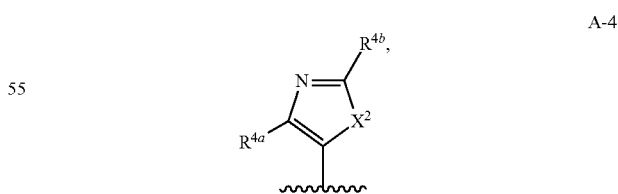

A-4

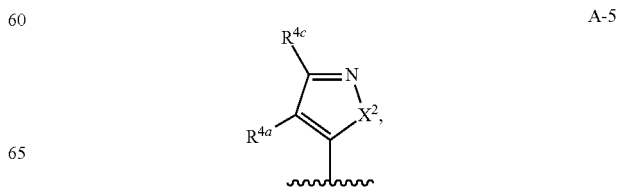

A-5

-continued

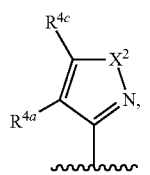

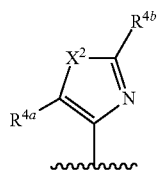

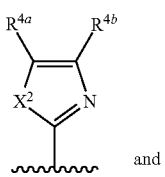 and

-continued

A-6

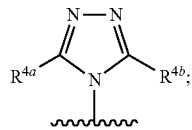

A-7

A-8

A-9

$R^{4a}$, $R^{4b}$, and $R^{4c}$ are each independently selected from the group consisting of hydrogen, halo, haloalkyl, and alkyl; $X^2$ is selected from the group consisting of —O—, —S—, and —N($R^{5c1}$)—; and $R^{5c1}$ is selected from the group consisting of hydrogen and alkyl. In another embodiment, A is:

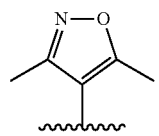

In another embodiment, Compounds of the Disclosure are compounds of Table 1, and the pharmaceutically acceptable salts, hydrates, and solvates thereof.

TABLE 1

| Cpd. No. | Structure | Name |
| --- | --- | --- |
| 1 | 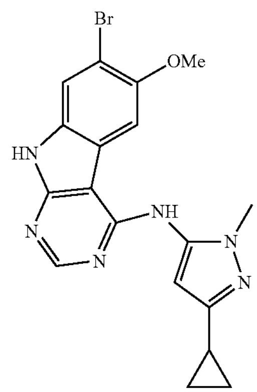 [SMILES: COc1cc2c(cc1Br)[nH]c1ncnc(Nc3cc(C4CC4)nn3C)c12] | 7-bromo-N-(3-cyclopropyl-1-methyl-1H-pyrazol-5-yl)-6-methoxy-9H-pyrimido[4,5-b]indol-4-amine |
| 2 | 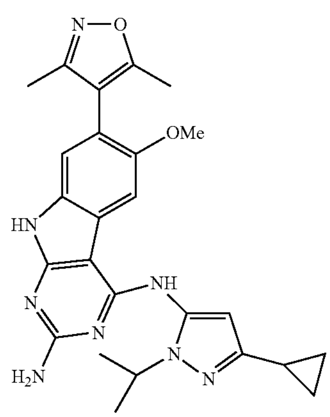 [SMILES: COc1cc2c(cc1-c1c(C)noc1C)[nH]c1nc(N)nc(Nc3cc(C4CC4)nn3C(C)C)c12] | N4-(3-cyclopropyl-1-isopropyl-1H-pyrazol-5-yl)-7-(3,5-dimethylisoxazol-4-yl)-6-methoxy-9H-pyrimido[4,5-b]indole-2,4-diamine |

TABLE 1-continued

| Cpd. No. | Structure | Name |
|---|---|---|
| 3 | 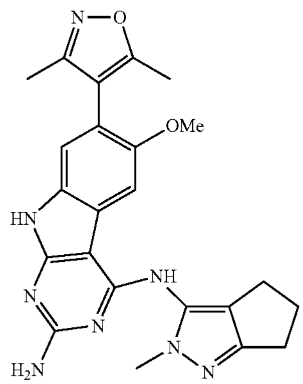 [SMILES: COc1cc2c(cc1-c1c(C)noc1C)[nH]c1nc(N)nc(Nc3c4c(nn3C)CCC4)c12] | 7-(3,5-dimethylisoxazol-4-yl)-6-methoxy-N4-(2-methyl-2,4,5,6-tetrahydrocyclopenta[c]pyrazol-3-yl)-9H-pyrimido[4,5-b]indole-2,4-diamine |
| 4 | 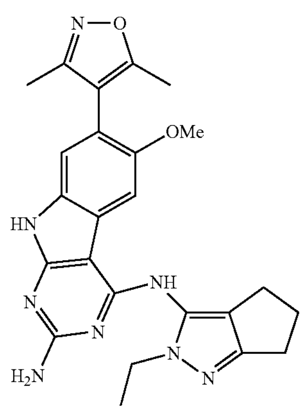 [SMILES: CCn1nc2c(c1Nc1nc(N)nc3[nH]c4cc(-c5c(C)noc5C)c(OC)cc4c13)CCC2] | 7-(3,5-dimethylisoxazol-4-yl)-N4-(2-ethyl-2,4,5,6-tetrahydrocyclopenta[c]pyrazol-3-yl)-6-methoxy-9H-pyrimido[4,5-b]indole-2,4-diamine |
| 5 | 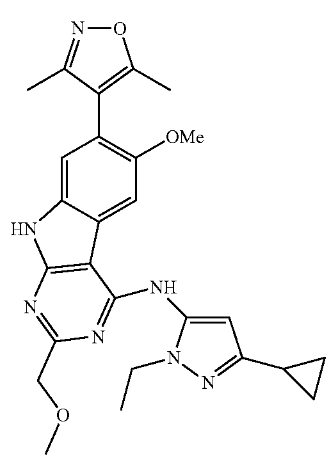 [SMILES: CCn1nc(C2CC2)cc1Nc1nc(COC)nc2[nH]c3cc(-c4c(C)noc4C)c(OC)cc3c12] | N-(3-cyclopropyl-1-ethyl-1H-pyrazol-5-yl)-7-(3,5-dimethylisoxazol-4-yl)-6-methoxy-2-(methoxymethyl)-9H-pyrimido[4,5-b]indole-amine |

TABLE 1-continued

| Cpd. No. | Structure | Name |
|---|---|---|
| 6 | 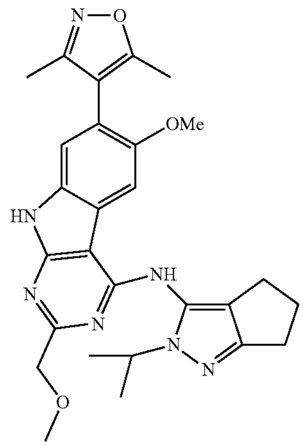 [SMILES: COCc1nc(Nc2c3c(nn2C(C)C)CCC3)c2c(n1)[nH]c1cc(-c3c(C)noc3C)c(OC)cc12] | 7-(3,5-dimethylisoxazol-4-yl)-N-(2-isopropyl-2,4,5,6-tetrahydrocyclopenta[c]pyrazol-3-yl)-6-methoxy-2-(methoxymethyl)-9H-pyrimido[4,5-b]indol-4-amine |
| 7 | 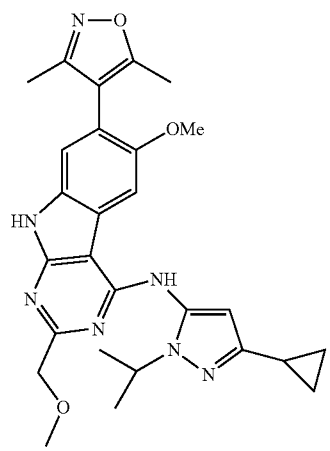 [SMILES: COCc1nc(Nc2cc(C3CC3)nn2C(C)C)c2c(n1)[nH]c1cc(-c3c(C)noc3C)c(OC)cc12] | N-(3-cyclopropyl-1-isopropyl-1H-pyrazol-5-yl)-7-(3,5-dimethylisoxazol-4-yl)-6-methoxy-2-(methoxymethyl)-9H-pyrimido[4,5-b]indol-4-amine |
| 8 | 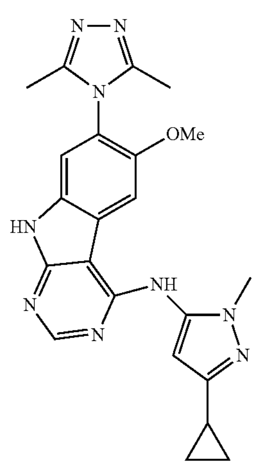 | N-(3-cyclopropyl-1-methyl-1H-pyrazol-5-yl)-7-(3,5-dimethyl-4H-1,2,4-triazol-4-yl)-6-methoxy-9H-pyrimido[4,5-b]indol-4-amine |

TABLE 1-continued

| Cpd. No. | Structure | Name |
|---|---|---|
| 9 | 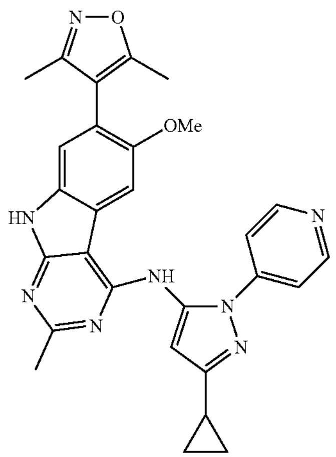 [SMILES: COc1cc2c(cc1-c1c(C)noc1C)[nH]c1nc(C)nc(Nc3cc(C4CC4)nn3-c3ccncc3)c12] | N-(3-cyclopropyl-1-(pyridin-4-yl)-1H-pyrazol-5-yl)-7-(3,5-dimethylisoxazol-4-yl)-6-methoxy-2-methyl-9H-pyrimido[4,5-b]indol-4-amine |
| 10 | 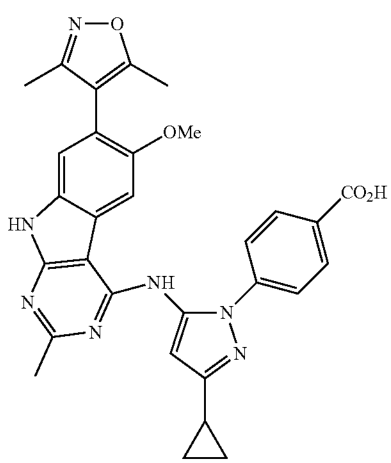 [SMILES: COc1cc2c(cc1-c1c(C)noc1C)[nH]c1nc(C)nc(Nc3cc(C4CC4)nn3-c3ccc(C(=O)O)cc3)c12] | 4-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)benzoic acid |
| 11 | 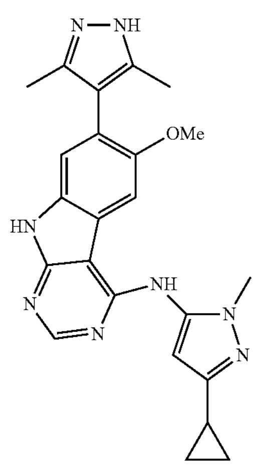 | N-(3-cyclopropyl-1-methyl-1H-pyrazol-5-yl)-7-(3,5-dimethyl-1H-pyrazol-4-yl)-6-methoxy-9H-pyrimido[4,5-b]indol-4-amine |

TABLE 1-continued

| Cpd. No. | Structure | Name |
| --- | --- | --- |
| 12 | 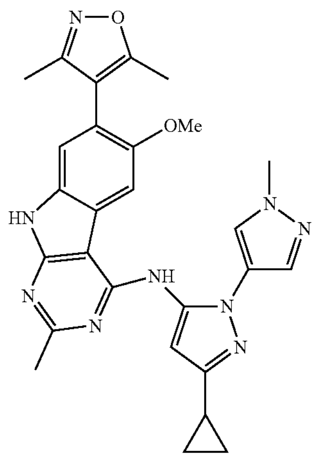 [SMILES: COc1cc2c(cc1-c1c(C)noc1C)[nH]c1nc(C)nc(Nc3cc(C4CC4)nn3-c3cnn(C)c3)c12] | N-(3-cyclopropyl-1'-methyl-1'H-[1,4'-bipyrazol]-5-yl)-7-(3,5-dimethylisoxazol-4-yl)-6-methoxy-2-methyl-9H-pyrimido[4,5-b]indol-4-amine |
| 13 | 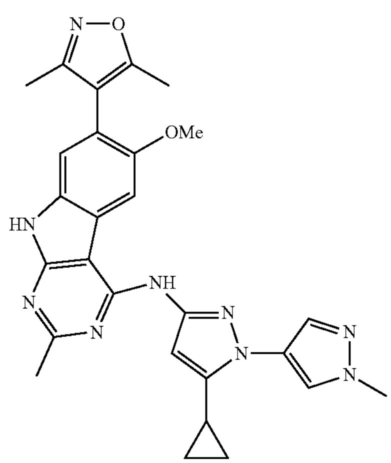 | N-(5-cyclopropyl-1'-methyl-1'H-[1,4'-bipyrazol]-3-yl)-7-(3,5-dimethylisoxazol-4-yl)-6-methoxy-2-methyl-9H-pyrimido[4,5-b]indol-4-amine |
| 14 | 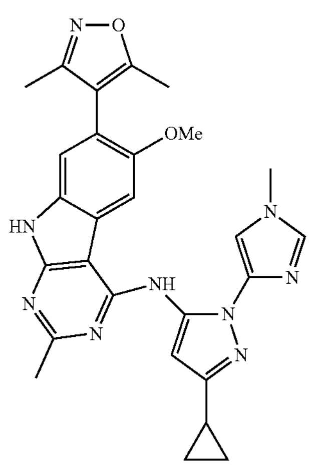 [SMILES: COc1cc2c(cc1-c1c(C)noc1C)[nH]c1nc(C)nc(Nc3cc(C4CC4)nn3-c3cn(C)cn3)c12] | N-(3-cyclopropyl-1-(1-methyl-1H-imidazol-4-yl)-1H-pyrazol-5-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
|---|---|---|
| 15 | 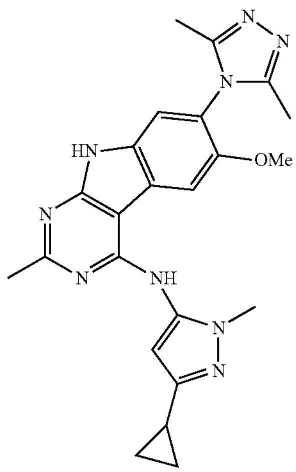 | N-(3-cyclopropyl-1-methyl-1H-pyrazol-5-yl)-7-(3,5-dimethyl-4H-1,2,4-triazol-4-yl)-6-methoxy-2-methyl-9H-pyrimido[4,5-b]indol-4-amine |
| 16 | 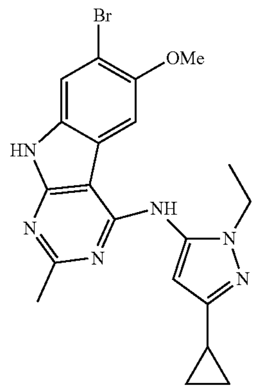 [SMILES: CCn1nc(C2CC2)cc1Nc1nc(C)nc2[nH]c3cc(Br)c(OC)cc3c12] | 7-bromo-N-(3-cyclopropyl-1-ethyl-1H-pyrazol-5-yl)-6-methoxy-2-methyl-9H-pyrimido[4,5-b]indol-4-amine |
| 17 | 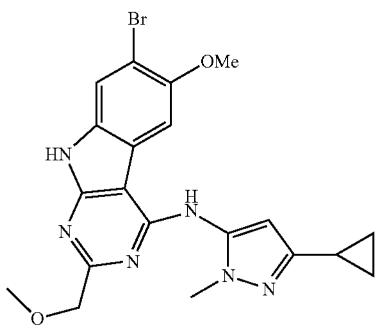 [SMILES: COCc1nc(Nc2cc(C3CC3)nn2C)c2c(n1)[nH]c1cc(Br)c(OC)cc12] | 7-bromo-N-(3-cyclopropyl-1-methyl-1H-pyrazol-5-yl)-6-methoxy-2-(methoxymethyl)-9H-pyrimido[4,5-b]indol-4-amine |
| 18 | 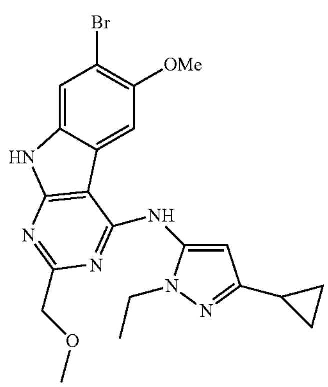 [SMILES: CCn1nc(C2CC2)cc1Nc1nc(COC)nc2[nH]c3cc(Br)c(OC)cc3c12] | 7-bromo-N-(3-cyclopropyl-1-ethyl-1H-pyrazol-5-yl)-6-methoxy-2-(methoxymethyl)-9H-pyrimido[4,5-b]indole-amine |

TABLE 1-continued

| Cpd. No. | Structure | Name |
|---|---|---|
| 19 | 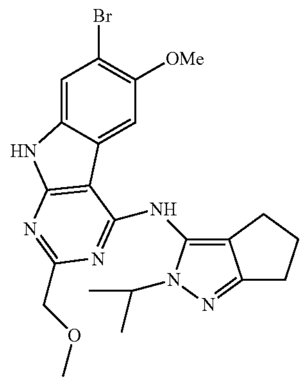 [SMILES: COCc1nc(Nc2c3c(nn2C(C)C)CCC3)c2c(n1)[nH]c1cc(Br)c(OC)cc12] | 7-bromo-N-(2-isopropyl-2,4,5,6-tetrahydrocyclopenta[c]pyrazol-3-yl)-6-methoxy-2-(methoxymethyl)-9H-pyrimido[4,5-b]indol-4-amine |
| 20 | 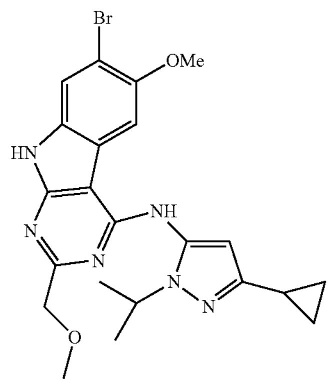 [SMILES: COCc1nc(Nc2cc(C3CC3)nn2C(C)C)c2c(n1)[nH]c1cc(Br)c(OC)cc12] | 7-bromo-N-(3-cyclopropyl-1-isopropyl-1H-pyrazol-5-yl)-6-methoxy-2-(methoxymethyl)-9H-pyrimido[4,5-b]indol-4-amine |
| 21 | 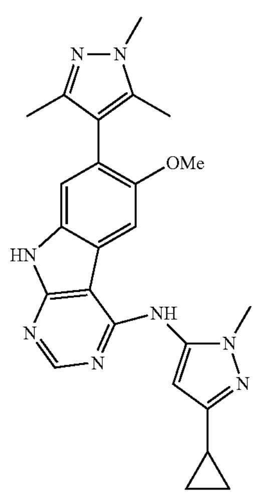 | N-(3-cyclopropyl-1-methyl-1H-pyrazol-5-yl)-6-methoxy-7-(1,3,5-trimethyl-1H-pyrazol-4-yl)-9H-pyrimido[4,5-b]indol-4-amine |

In another embodiment, Compounds of the Disclosure are compounds of selected from the group consisting of:

N-(3-cyclopropyl-1-ethyl-1H-pyrazol-5-yl)-7-(3,5-dimethylisoxazol-4-yl)-6-methoxy-2-(methoxymethyl)-9H-pyrimido[4,5-b]indol-4-amine;

7-(3,5-dimethylisoxazol-4-yl)-N-(2-isopropyl-2,4,5,6-tetrahydrocyclopenta[c]pyrazol-3-yl)-6-methoxy-2-(methoxymethyl)-9H-pyrimido[4,5-b]indol-4-amine; and N-(3-cyclopropyl-1-isopropyl-1H-pyrazol-5-yl)-7-(3,5-dimethylisoxazol-4-yl)-6-methoxy-2-(methoxymethyl)-9H-pyrimido[4,5-b]indol-4-amine, and the pharmaceutically acceptable salts, hydrates, and solvates thereof.

In another embodiment, the present disclosure provides methods of preparing a compound represented by Formula VII:

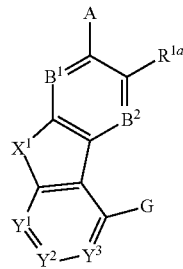

VII and the pharmaceutically acceptable salts, hydrates, and solvates thereof, wherein $R^{1a}$, A, $B^1$, $B^2$, G, $X^1$, $Y^1$, $Y^2$, and $Y^3$ are as defined above in connection with Formula I, with the proviso that A is not 1,3-dimethyl-1H-pyrazol-4-yl, or:

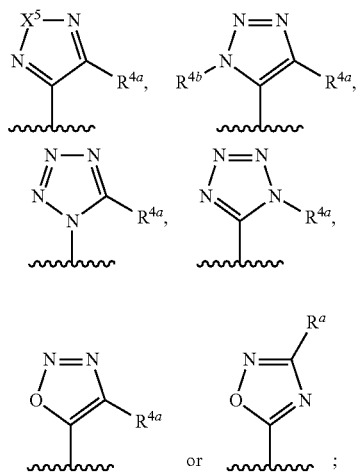

wherein:

$R^{4a}$ and $R^{4b}$ are each independently selected from the group consisting of hydrogen, halo, haloalkyl, and alkyl.

In another embodiment, the method of preparing a compound represented by Formula VII comprises reacting a compound represented by Formula VIII:

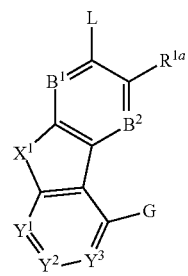

VIII and the pharmaceutically acceptable salts, hydrates, and solvates thereof, wherein $R^{1a}$, $B^1$, $B^2$, G, L, $X^1$, $Y^1$, $Y^2$, and $Y^3$ are as defined above in connection with Formula I, with a compound having Formula IX:

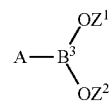

IX wherein:
  A is optionally substituted 5-membered heteroaryl;
  $B^3$ is boron;
  $Z^1$ is selected from the group consisting of hydrogen and alkyl; and
  $Z^2$ is selected from the group consisting of hydrogen and alkyl; or
  $Z^1$ and $Z^2$ taken together form a linkage —(CR'R")$_p$—;
wherein:
  each R' is independently selected from the group consisting of hydrogen and alkyl;
  each R" is independently selected from the group consisting of hydrogen and alkyl; and
  p is 2, 3, or 4,
  with the proviso that when G is —Z—$R^3$ and $R^3$ is 3-cyclopropyl-1-methyl-1H-pyrazol-5-yl, then L is not Br.

In another embodiment, the present disclosure provides methods of preparing a compound represented by Formula X:

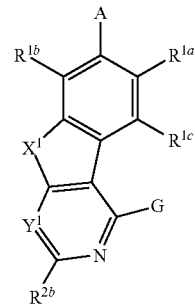

X and the pharmaceutically acceptable salts, hydrates, and solvates thereof, wherein $R^{1a}$, $R^{1b}$, $R^{1c}$, $R^{2b}$, A, G, $X^1$, and $Y^1$ are as defined above in connection with Formula II, with the proviso that A is not 1,3-dimethyl-1H-pyrazol-4-yl, or:

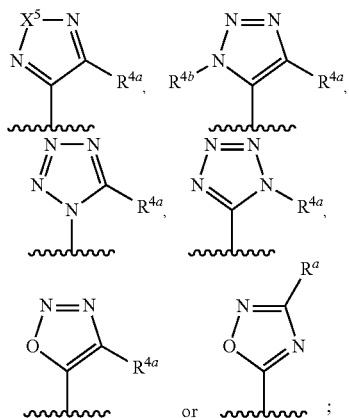

wherein:

$R^{4a}$ and $R^{4b}$ are each independently selected from the group consisting of hydrogen, halo, haloalkyl, and alkyl.

In another embodiment, the method comprises reacting a compound represented by Formula XI:

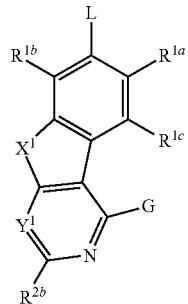

XI and the pharmaceutically acceptable salts, hydrates, and solvates thereof, wherein $R^{1a}$, $R^{1b}$, $R^{1c}$, $R^{2b}$, L, G, $X^1$, and $Y^1$ are as defined above in connection with Formula II, with a compound having Formula IX as defined above, with the proviso with the proviso that when G is —Z—$R^3$ and $R^3$ is 3-cyclopropyl-1-methyl-1H-pyrazol-5-yl, then L is not Br.

In another embodiment, the present disclosure provides methods of preparing a compound represented by Formula XII:

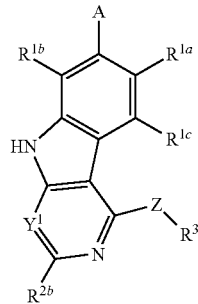

XII and the pharmaceutically acceptable salts, hydrates, and solvates thereof, wherein $R^{1a}$, $R^{1b}$, $R^{1c}$, $R^{2b}$, $R^3$, A, $Y^1$, and Z are as defined above in connection with Formula III, with the proviso that A is not 1,3-dimethyl-1H-pyrazol-4-yl, or:

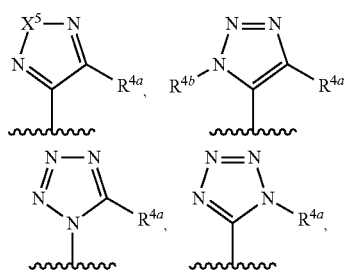

-continued

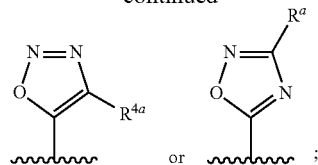

or ;

wherein:

$R^{4a}$ and $R^{4b}$ are each independently selected from the group consisting of hydrogen, halo, haloalkyl, and alkyl.

In another embodiment, the method comprises reacting a compound represented by Formula XIII:

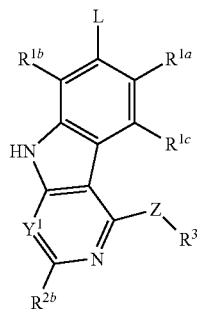

XIII and the pharmaceutically acceptable salts, hydrates, and solvates thereof, wherein $R^{1a}$, $R^{1b}$, $R^{1c}$, $R^{2b}$, $R^3$, L, $Y^1$, and Z are as defined above in connection with Formula III, with a compound having Formula IX as defined above, with the proviso that when G is —Z—$R^3$ and $R^3$ is 3-cyclopropyl-1-methyl-1H-pyrazol-5-yl, then L is not Br.

In another embodiment, the present disclosure provides methods of preparing a compound represented by Formula XIV:

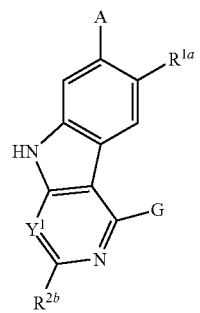

XIV and the pharmaceutically acceptable salts, hydrates, and solvates thereof, wherein $R^{1a}$, $R^{2b}$, A, G, and $Y^1$ are as defined above in connection with Formula IV, with the proviso that A is not 1,3-dimethyl-1H-pyrazol-4-yl, or:

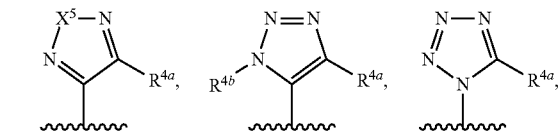

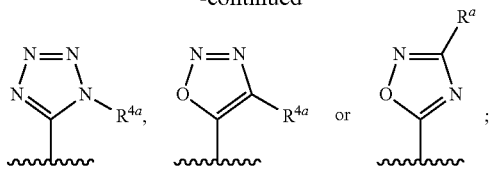

wherein:
$R^{4a}$ and $R^{4b}$ are each independently selected from the group consisting of hydrogen, halo, haloalkyl, and alkyl.

In another embodiment, the method comprises reacting a compound represented by Formula XV:

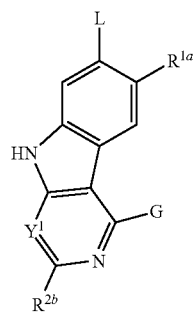

XV and the pharmaceutically acceptable salts, hydrates, and solvates thereof, wherein $R^{1a}$, $R^{2b}$, L, G, and $Y^1$ are as defined above in connection with Formula IV, with a compound having Formula IX as defined above, with the proviso that when G is —Z—$R^3$ and $R^3$ is 3-cyclopropyl-1-methyl-1H-pyrazol-5-yl, then L is not Br.

In another embodiment, the present disclosure provides a method of preparing a compound represented by Formula XVI:

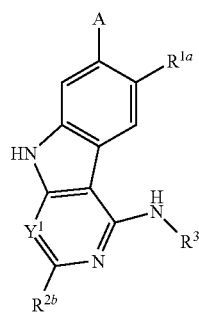

XVI and the pharmaceutically acceptable salts, hydrates, and solvates thereof, wherein $R^{1a}$ $R^{2b}$, $R^3$, A, and $Y^1$ are as defined above in connection with Formula V,
with the proviso that A is not 1,3-dimethyl-1H-pyrazol-4-yl, or:

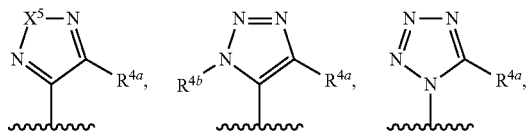

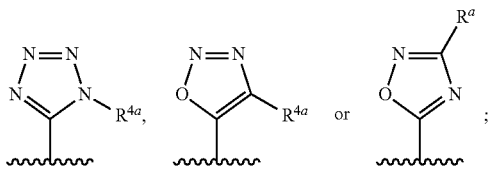

wherein:
$R^{4a}$ and $R^{4b}$ are each independently selected from the group consisting of hydrogen, halo, haloalkyl, and alkyl.

In another embodiment, the method comprises reacting a compound represented by Formula XVII:

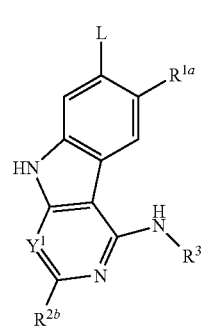

XVII and the pharmaceutically acceptable salts, hydrates, and solvates thereof, wherein $R^{1a}$, $R^{2b}$, $R^3$, L, and $Y^1$ are as defined above in connection with Formula V, with a compound having Formula IX as defined above, with the proviso that when G is —Z—$R^3$ and $R^3$ is 3-cyclopropyl-1-methyl-1H-pyrazol-5-yl, then L is not Br.

In another embodiment, the present disclosure provides methods of preparing a compound represented by Formula XVIII:

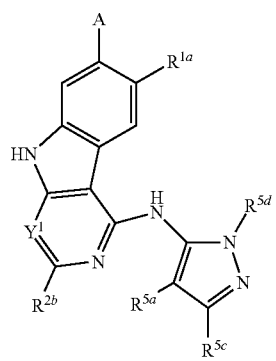

XVIII and the pharmaceutically acceptable salts, hydrates, and solvates thereof, wherein $R^{1a}$, $R^{2b}$, $R^{5a}$, $R^{5c}$, $R^{5d}$, $Y^1$, and A are as defined above in connection with Formula VI,
with the proviso that A is not 1,3-dimethyl-1H-pyrazol-4-yl, or:

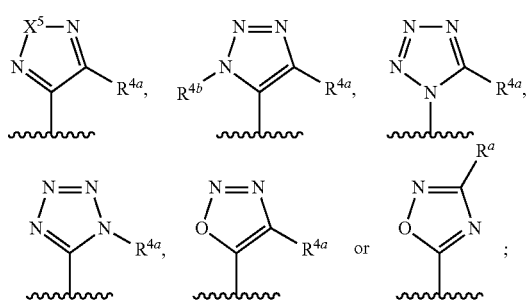

wherein:

$R^{4a}$ and $R^{4b}$ are each independently selected from the group consisting of hydrogen, halo, haloalkyl, and alkyl.

In another embodiment, the method comprises reacting a compound represented by Formula XIX:

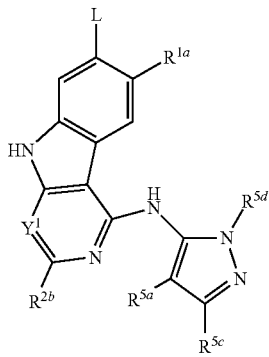

XIX and the pharmaceutically acceptable salts, hydrates, and solvates thereof, wherein $R^{1a}$, $R^{2b}$, $R^{5a}$, $R^{5c}$, $R^{5d}$, $Y^1$, and L are as defined above in connection with Formula VI, with a compound having Formula IX as defined above, with the proviso that when G is —Z—$R^3$ and $R^3$ is 3-cyclopropyl-1-methyl-1H-pyrazol-5-yl, then L is not Br.

In another embodiment, the methods described above further comprises isolating the compound represented by any one of Formulae VII, X, XII, XIV, XVI, and XVIII, e.g., free from starting materials, reagents, solvents, and/or reaction side-products. In another embodiment, the reaction is carried out in a solvent, e.g., dimethylformamide, acetonitrile, dimethyl sulfoxide, and/or N-methyl-2-pyrrolidone. In another embodiment, the reaction is carried out at a temperature of about 50° C. to about 200° C., e.g., at about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., or about 200° C.

In another embodiment, the methods described above comprises reacting a compound having Formula VIII, XI, XIII, XV, XVII, or XIX wherein L is —$OSO_2CF_3$.

In another embodiment, the methods described above comprises reacting a compound having Formula VIII, XI, XIII, XV, XVII, or XIX, wherein L is —$OSO_2CF_3$, with a compound having Formula IX, wherein $Z^1$ and $Z^2$ taken together form a linkage —$(CR'R'')_p$—. In another embodiment, the linkage is —$C(CH_3)_2C(CH_3)_2$—.

Compounds of the Disclosure inhibit BET bromodomains and are useful in the treatment of a variety of diseases and conditions. In particular, Compounds of the Disclosure are useful in methods of treating a disease or condition wherein inhibition of BET bromodomains provides a benefit, for example, cancers and proliferative diseases. Methods of the disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

Salts, hydrates, and solvates of the Compounds of the Disclosure can also be used in the methods disclosed herein. The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem. Commun.* 603-604 (2001). A typical, nonlimiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as BET bromodomain inhibitors for the treatment of a variety of diseases and conditions wherein inhibition of BET bromodomains has a beneficial effect. Compounds of the Disclosure typically have a binding affinity ($IC_{50}$) to BET bromodomains of less than 100 μM, e.g., less than 50 μM, less than 25 μM, and less than 5 μM, less than about 1 μM, less than about 0.5 μM, or less than about 0.1 μM. In one embodiment, the present disclosure relates to a method of treating an individual suffering from a disease or condition wherein inhibition of the BET bromodomains provides a benefit comprising administering a therapeutically effective amount of a Compound of the Disclosure to an individual in need thereof.

Since Compounds of the Disclosure are inhibitors of one or more BET bromodomains, a number of diseases and conditions mediated by BET bromodomain proteins can be treated by employing these compounds. The present disclosure is thus directed generally to a method for treating a condition or disorder responsive to inhibition of BRD2, BRD3, BRD4, BRD-t, or an isoform or mutant thereof, in an animal, e.g., a human, suffering from, or at risk of suffering from, the condition or disorder, the method comprising administering to the animal an effective amount of one or more Compounds of the Disclosure.

The present disclosure is further directed to a method of inhibiting BET bromodomains in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent useful in the treatment of diseases and conditions wherein inhibition of BET bromodomains provides a benefit, packaged separately or together, and an insert having instructions for using these active agents.

In one embodiment, a Compound of the Disclosure is administered in conjunction with a second therapeutic agent useful in the treatment of a disease or condition wherein inhibition of BET bromodomains provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit BET bromodomain activity in the patient.

In one embodiment, the disease to be treated by the Compound of the Disclosure is cancer. Examples of treatable cancers include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In another embodiment, the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the BET bromodomain inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransyl-cytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Ax1 receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present BET bromodomain inhibitor, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present BET bromodomain inhibitor also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compound of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

The term "BET bromodomain" as used herein means one or more of BRD2, BRD3, BRD4, and BRD-t, or an isoform or mutant thereof.

The term "a disease or condition wherein inhibition of BET bromodomains provides a benefit" pertains to a condition in which at least one of BRD2, BRD3, BRD4, and BRD-t, and/or an action of at least one of BRD2, BRD3, BRD4, and BRD-t, is important or necessary, e.g., for the onset, progress, expression of that disease or condition, or a disease or a condition which is known to be treated by a BET bromodomain inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a BET bromodomain for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a Compound of the Disclosure is a potent inhibitor of BET bromodomains and can be used in treating diseases and conditions wherein inhibition of BET bromodomains provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce BET bromodomain signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

For the purpose of the present disclosure, the term "leaving group" refers to an atom or group of atoms that becomes detached from an atom or group of atoms in what is considered to be the residual or main part of the molecule in a specified reaction. Non-limiting exemplary leaving groups include —Cl, —I, —Br, —OTf, -OMs, and -OTs.

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2SO_2CH_3CH_2CH_2CO_2H$, —$CH_2CH_2SO_2CH_3$, —$CH_2CH_2COPh$, and —$CH_2C_6H_{11}$.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and cyclopentenyl, cyclohexenyl.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups, e.g.,

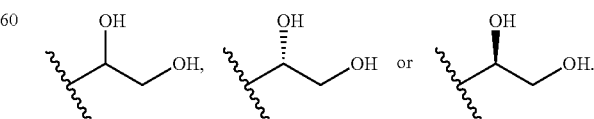

In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —$SCH_3$, and —$SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino) alkyl, (carboxamido)alkyl, mercaptoalkyl, or (heterocyclo) alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

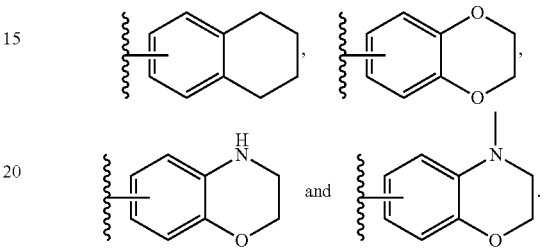

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "aralkyloxy" as used by itself or as part of another group refers to an aralkyl group attached to a terminal oxygen atom. A non-limiting exemplary aralkyloxy group is $PhCH_2O$—.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. In one embodiment, the heteroalkyl contains one oxygen and one nitrogen atom. In one embodiment, the heteroalkyl contains two nitrogen atoms. Non-limiting exemplary heteroalkyl groups include —$CH_2OCH_2CH_2OCH_3$, —$OCH_2CH_2OCH_2CH_2OCH_3$, —$CH_2NHCH_2CH_2OCH_3$, —$OCH_2CH_2NH_2$, —$NHCH_2CH_2N(H)CH_3$, —$NHCH_2CH_2OCH_3$ and —$OCH_2CH_2OCH_3$.

For the purpose of the present disclosure, the term "heteroaryl" or "heteroaromatic" refers to monocyclic and bicyclic aromatic ring systems having 5 to 14 ring atoms (i.e., $C_5$-$C_{14}$ heteroaryl), wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. In one embodiment, the optionally substituted heteroaryl has one substituent. Any available carbon or nitrogen atom can be substituted. Non-limiting exemplary optionally substituted 5-membered heteroaryl groups include, but are not limited to:

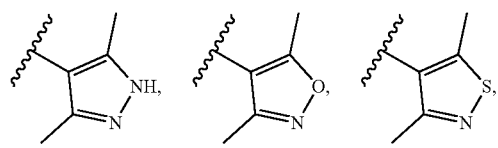

-continued

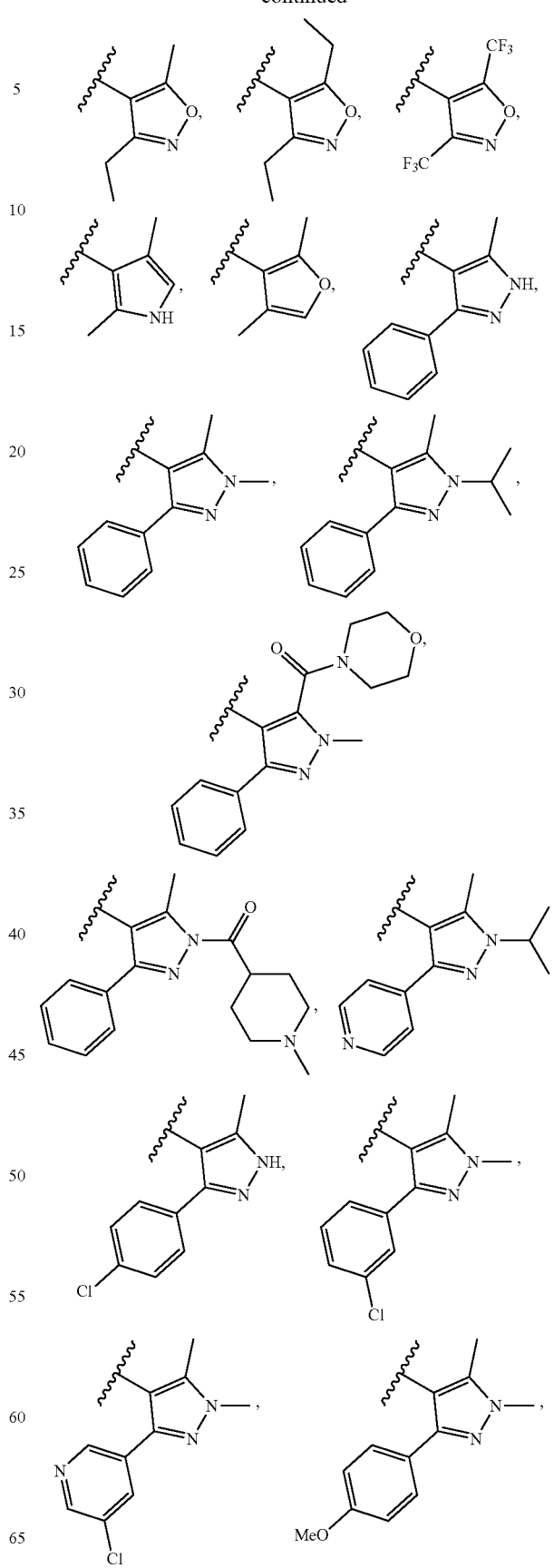

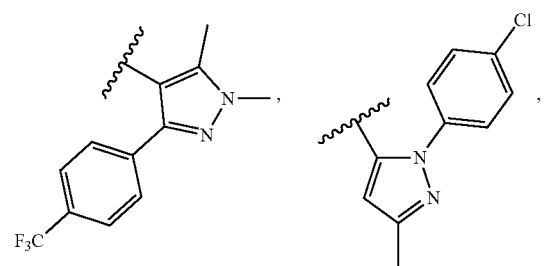
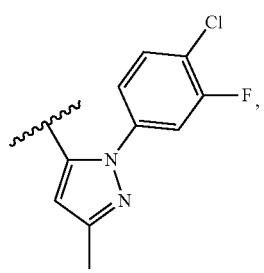
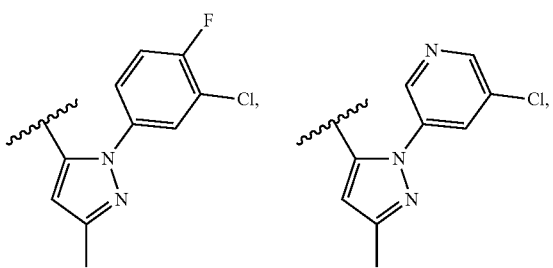
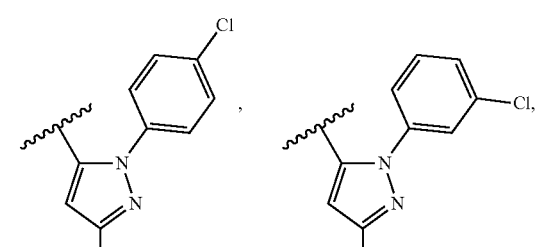
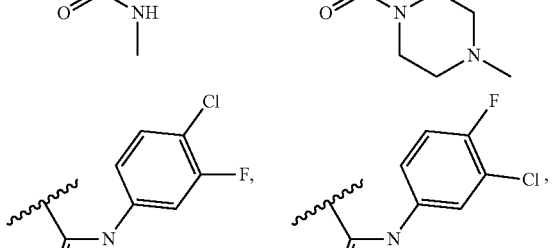
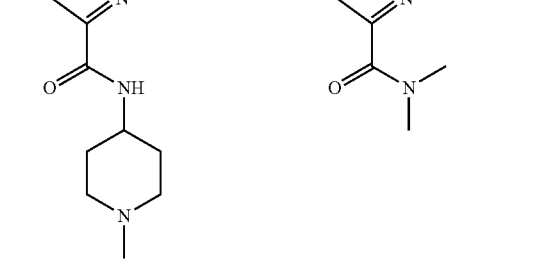
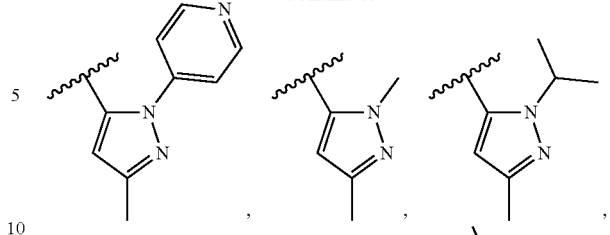

The term optionally substituted heteroaryl is also meant to include groups having fused optionally substituted cycloalkyl and fused optionally substituted heterocyclo rings. Non-limiting examples include:

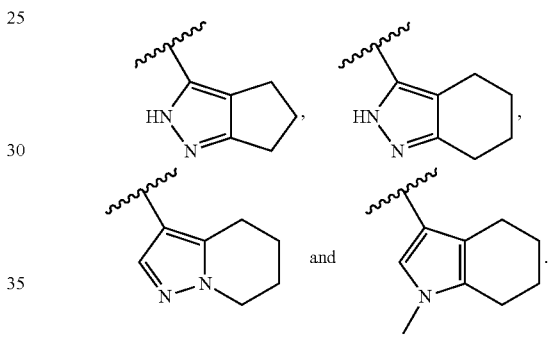

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl, chroman-4-yl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, $CF_3C(=O)$—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary optionally substituted heterocyclo groups include:

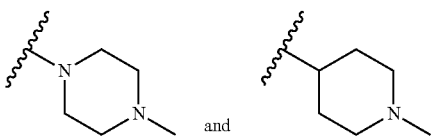

For the purpose of the present disclosure, the term "amino" as used by itself or as part of another group refers to $-NR^{7a}R^{7b}$, wherein $R^{7a}$ and $R^{7b}$ are each independently hydrogen, alkyl, hydroxyalkyl, optionally substituted cycloalkyl, optionally substituted aryl, optionally substituted heterocyclo, or optionally substituted heteroaryl, or $R^{7a}$ and $R^{7b}$ are taken together to form a 3- to 8-membered optionally substituted heterocyclo. Non-limiting exemplary amino groups include $-NH_2$ and $-N(H)(CH_3)$.

For the purpose of the present disclosure, the term "(amino)alkyl" as used by itself or as part of another group refers to an alkyl group substituted with an amino group. Non-limiting exemplary amino alkyl groups include $-CH_2CH_2NH_2$, and $-CH_2CH_2N(H)CH_3$, $-CH_2CH_2N(CH_3)_2$, and $-CH_2N(H)$cyclopropyl.

For the purpose of the present disclosure, the term "carboxamido" as used by itself or as part of another group refers to a radical of formula $-C(=O)NR^{9a}R^{9b}$, wherein $R^{9a}$ and $R^{9b}$ are each independently hydrogen, optionally substituted alkyl, hydroxyalkyl, optionally substituted cycloalkyl, optionally substituted aryl, optionally substituted heterocyclo, or optionally substituted heteroaryl, or $R^{9a}$ and $R^{9b}$ taken together with the nitrogen to which they are attached form a 3- to 8-membered optionally substituted heterocyclo group. In one embodiment, $R^{9a}$ and $R^{9b}$ are each independently hydrogen or optionally substituted alkyl. In one embodiment, $R^{9a}$ and $R^{9b}$ are taken together to taken together with the nitrogen to which they are attached form a 3- to 8-membered optionally substituted heterocyclo group. Non-limiting exemplary carboxamido groups include, but are not limited to, $-CONH_2$, $-CON(H)CH_3$, $-CON(CH_3)_2$, $-CON(H)Ph$,

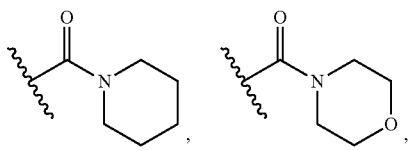

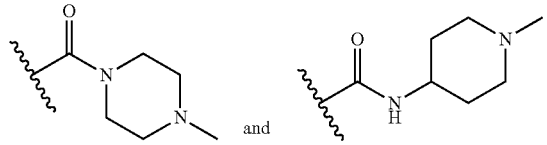

For the purpose of the present disclosure, the term "sulfonamido" as used by itself or as part of another group refers to a radical of the formula $-SO_2NR^{8a}R^{8b}$, wherein $R^{8a}$ and $R^{8b}$ are each independently hydrogen, optionally substituted alkyl, or optionally substituted aryl, or $R^{8a}$ and $R^{8b}$ taken together with the nitrogen to which they are attached from a 3- to 8-membered heterocyclo group. Non-limiting exemplary sulfonamido groups include $-SO_2NH_2$, $-SO_2N(H)CH_3$, and $-SO_2N(H)Ph$.

For the purpose of the present disclosure, the term "alkylcarbonyl" as used by itself or as part of another group refers to a carbonyl group, i.e., $-C(=O)$—, substituted by an alkyl group. A non-limiting exemplary alkylcarbonyl group is $-COCH_3$.

For the purpose of the present disclosure, the term "arylcarbonyl" as used by itself or as part of another group refers to a carbonyl group, i.e., $-C(=O)$—, substituted by an optionally substituted aryl group. A non-limiting exemplary arylcarbonyl group is $-COPh$.

For the purpose of the present disclosure, the term "alkoxycarbonyl" as used by itself or as part of another group refers to a carbonyl group, i.e., $-C(=O)$—, substituted by an alkoxy group. Non-limiting exemplary alkoxycarbonyl groups include $-C(=O)OMe$, $-C(=O)OEt$, and $-C(=O)OtBu$.

For the purpose of the present disclosure, the term "alkylsulfonyl" as used by itself or as part of another group refers to a sulfonyl group, i.e., $-SO_2$—, substituted by any of the above-mentioned optionally substituted alkyl groups. A non-limiting exemplary alkylsulfonyl group is $-SO_2CH_3$.

For the purpose of the present disclosure, the term "arylsulfonyl" as used by itself or as part of another group refers to a sulfonyl group, i.e., $-SO_2$—, substituted by any of the above-mentioned optionally substituted aryl groups. A non-limiting exemplary arylsulfonyl group is $-SO_2Ph$.

For the purpose of the present disclosure, the term "mercaptoalkyl" as used by itself or as part of another group refers to any of the above-mentioned alkyl groups substituted by a $-SH$ group.

For the purpose of the present disclosure, the term "carboxy" as used by itself or as part of another group refers to a radical of the formula $-COOH$.

For the purpose of the present disclosure, the term "carboxyalkyl" as used by itself or as part of another group refers to any of the above-mentioned alkyl groups substituted with a $-COOH$. A non-limiting exemplary carboxyalkyl group is $-CH_2CO_2H$.

For the purpose of the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a $C_{1-4}$ alkyl substituted with one optionally substituted aryl group. In one embodiment, the optionally substituted aralkyl group is a $C_1$ or $C_2$ alkyl substituted with one optionally substituted aryl group. In one embodiment, the optionally substituted aralkyl group is a $C_1$ or $C_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

For the purpose of the present disclosure, the terms "(heterocyclo)alkyl" as used by itself or part of another group refers to an alkyl group substituted with an optionally substituted heterocyclo group. In one embodiment, the (heterocyclo)alkyl is a $C_{1-4}$ alkyl substituted with one optionally substituted heterocyclo group. Non-limiting exemplary (heterocyclo)alkyl groups include:

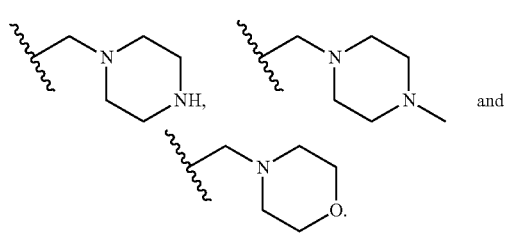

For the purpose of the present disclosure, the term "(carboxamido)alkyl" as used by itself or as part of another group refers to an alkyl group substituted with one or two carboxamido groups. In one embodiment, the (carboxamido)alkyl is a $C_{1-4}$ alkyl substituted with one carboxamido group. In another embodiment, the (carboxamido)alkyl is a $C_{1-4}$ alkyl substituted with two carboxamido groups. Non-limiting exemplary (carboxamido)alkyl groups include —CH$_2$CONH$_2$, —C(H)CH$_3$—CONH$_2$, —CH$_2$CON(H)CH$_3$, and —CH(CO$_2$NH$_2$)CH—$_2$CH$_2$CO$_2$NH$_2$.

EXAMPLES

Example 1

Synthesis of 7-Bromo-N-(3-cyclopropyl-1-methyl-1H-pyrazol-5-yl)-6-methoxy-9H-pyrimido[4,5-b]indol-4-amine (Cpd. No. 1)

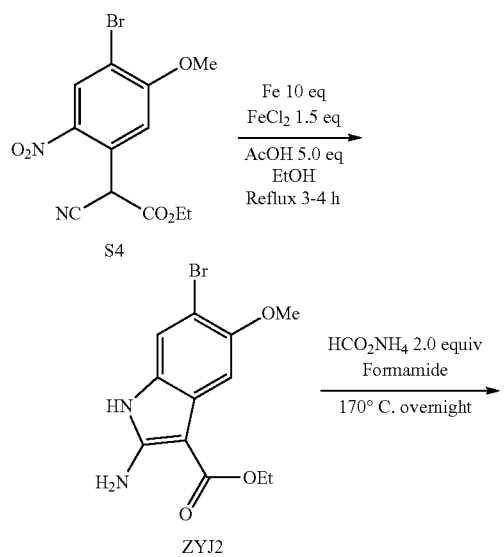

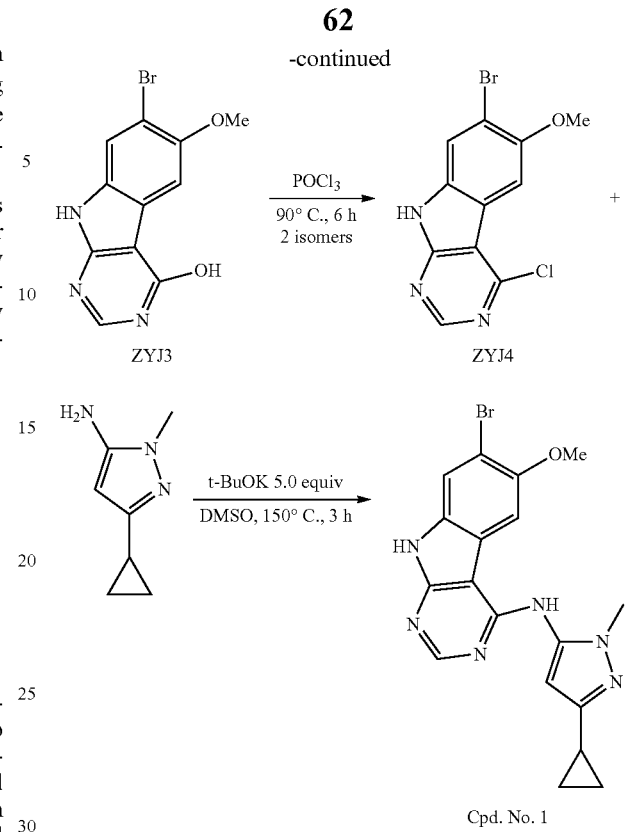

Step 1: S4 (5.85 g, 17 mmol), FeCl$_2$ (3.23 g, 25.5 mmol), and iron powder (9.52 g, 170 mmol) were mixed in a round-bottom flask and ethanol (200 mL) was added. Following that, acetic acid (2.1 g, 35 mmol) was added via a syringe and the mixture was heated at reflux for 3 h. The reaction mixture was diluted with ethyl acetate and filtered through a pad of Celite® and washed with ethyl acetate. The organic solutions were combined and concentrated on a rotary evaporator. The remaining residues was re-dissolved in ethyl acetate and washed with saturated aqueous sodium bicarbonate. The aqueous layer was extracted with ethyl acetate and organic layers were combined and washed with brine, dried over anhydrous sodium sulfate, and concentrated on a rotary evaporator. The remaining residues were purified by flash column chromatography to afford ZYJ2 in 4.33 g (81% yield). $^1$H NMR (300 MHz, DMSO-d6): 10.48 (s, 1H), 7.24 (s, 1H), 6.71 (s, 1H), 4.20 (q, J=7.04 Hz, 2H), 3.77 (s, 3H), 1.31 (t, J=7.07 Hz, 3H).

Step 2: ZYJ2 (4.33 g, 13.8 mmol) and ammonium formate (1.76 g, 28 mmol) were mixed in formamide (30 mL) and the mixture heated at 175° C. for overnight. The reaction mixture was cooled to room temperature and water was added. The solid was collected by filtration and dried over high vacuum for overnight. The product ZYJ3 was obtained in 2.34 g (56%).

Step 3: ZYJ3 (2.34 g, 7.9 mmol) was placed in a dry round-bottom flask and POCl$_3$ (20 mL) was added. The mixture was heated at 90° C. for 6 h. Volatile components were removed on a rotary evaporator and the mixture was the diluted with ethyl acetate and poured into saturated aqueous sodium bicarbonate. The solid was washed with water and dried over high vacuum for overnight affording the desired product ZYJ4 (1.20 g). The aqueous layer was extracted with ethyl acetate and organic layers were combined and washed with brine, dried over anhydrous sodium sulfate, and concentrated on a rotary evaporator. The remaining residues were also the desired product ZYJ4 (0.87 g). $^1$H NMR (400 MHz, MeOD-d4): 8.13 (s, 1H), 7.66 (s, 1H), 7.58 (s, 1H), 3.91 (s, 3H).

Step 4: ZYJ4 (0.8 g, 2.56 mmol), 3-cyclopropyl-1-methyl-1H-pyrazol-5-amine (700 mg, 5.12 mmol), and t-BuOK (1.4 g, 12.8 mmol) were mixed in a dry round-bottom flask. Anhydrous DMSO (20 mL) was added via a syringe and the mixture was heated at 150° C. for 3 h. The mixture was neutralized with $CF_3CO_2H$ and water (5 mL) was added. The solution was purified by reverse phase HPLC to yield the titled compound in 243 mg as a salt of $CF_3CO_2H$. $^1$H NMR (400 MHz, MeOD-d4): 8.47 (s, 1H), 7.77 (s, 1H), 7.55 (s, 1H), 6.19 (s, 1H), 3.95 (s, 3H), 3.77 (s, 3H), 2.02-1.92 (m, 1H), 1.04-0.96 (m, 2H), 0.82-0.76 (m, 2H). ESI-MS calculated for $C_{18}H_{18}{}^{79}BrN_6O$ [M+H]$^+$=413.07; Observed: 413.17.

Example 2

Synthesis of N-(3-cyclopropyl-1-methyl-1H-pyrazol-5-yl)-7-(3,5-dimethyl-1H-pyrazol-4-yl)-6-methoxy-9H-pyrimido[4,5-b]indol-4-amine (Cpd. No. 11)

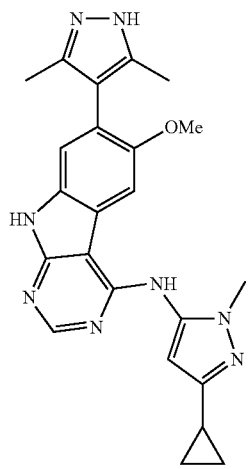

Cpd. No. 1 (50 mg, 0.1 mmol) and 3,5-dimethyl-4-(4,4,5,5-tetramethyl-1,3,2-dioxaborolan-2-yl)-1H-pyrazole (70 mg, 0.3 mmol) were dissolved in DME (6 mL), followed by addition of 2 M aqueous $Na_2CO_3$ (4 mL) via a syringe. The system was degassed and Pd(dppf)Cl$_2$—CH$_2$Cl$_2$ (40 mg, 0.05 mmol) was added. The reaction system was degassed again and refilled with nitrogen. The reaction heated at reflux for overnight. The aqueous layer was extracted with ethyl acetate, the combined organic layers were washed with brine, then dried over anhydrous $Na_2SO_4$. The volatile components were removed on a rotary evaporator and the residues were purified by reverse phase HPLC. The titled compound was isolated in 35 mg as a salt of $CF_3CO_2H$. $^1$H NMR (400 MHz, MeOD-d4): 8.53 (s, 1H), 7.74 (s, 1H), 7.58 (s, 1H), 6.20 (s, 1H), 3.94 (s, 3H), 3.81 (s, 3H), 2.02-1.93 (m, 1H), 1.05-0.97 (m, 2H), 0.82-0.76 (m, 2H). ESI-MS calculated for $C_{23}H_{25}N_8O$ [M+H]$^+$=429.22; Observed: 429.2

Example 3

Synthesis of N-(3-Cyclopropyl-1-methyl-1H-pyrazol-5-yl)-6-methoxy-7-(1,3,5-trimethyl-1H-pyrazol-4-yl)-9H-pyrimido[4,5-b]indol-4-amine (Cpd. No. 21)

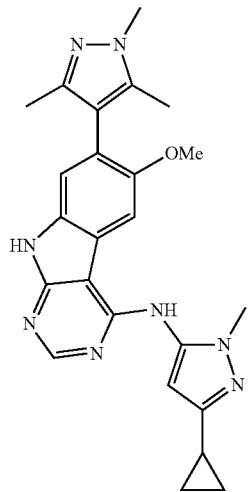

Cpd. No. 1 (50 mg, 0.1 mmol) and 1,3,5-trimethyl-4-(4,4,5,5-tetramethyl-1,3,2-dioxaborolan-2-yl)-1H-pyrazole (70 mg, 0.3 mmol) were dissolved in DME (6 mL), followed by addition of 2 M aqueous $Na_2CO_3$ (4 mL) via a syringe. The system was degassed and Pd(dppf)Cl$_2$—CH$_2$Cl$_2$ (40 mg, 0.05 mmol) was added. The reaction system was degassed again and refilled with nitrogen. The reaction heated at reflux for overnight. The aqueous layer was extracted with ethyl acetate, the combined organic layers were washed with brine, then dried over anhydrous $Na_2SO_4$. The volatile components were removed on a rotary evaporator and the residues were purified by reverse phase HPLC. The titled compound was isolated in 22.5 mg as a salt of $CF_3CO_2H$. $^1$H NMR (400 MHz, MeOD-d4): 8.51 (s, 1H), 7.70 (s, 1H), 7.50 (s, 1H), 6.19 (s, 1H), 3.95 (s, 3H), 3.92 (s, 3H), 3.79 (s, 3H), 2.27 (s, 3H), 2.24 (s, 3H), 2.02-1.93 (m, 1H), 1.05-0.95 (m, 2H), 0.83-0.75 (m, 2H). ESI-MS calculated for $C_{24}H_{27}N_8O$ [M+H]$^+$=443.23; Observed: 443.3.

Example 4

Synthesis of Synthesis of N-(3-Cyclopropyl-1-methyl-1H-pyrazol-5-yl)-7-(3,5-dimethyl-4H-1,2,4-triazol-4-yl)-6-methoxy-9H-pyrimido[4,5-b]indol-4-amine (Cpd. No. 8)

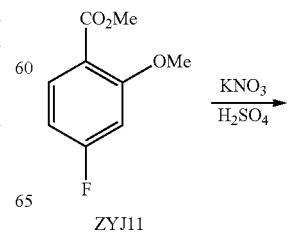

-continued
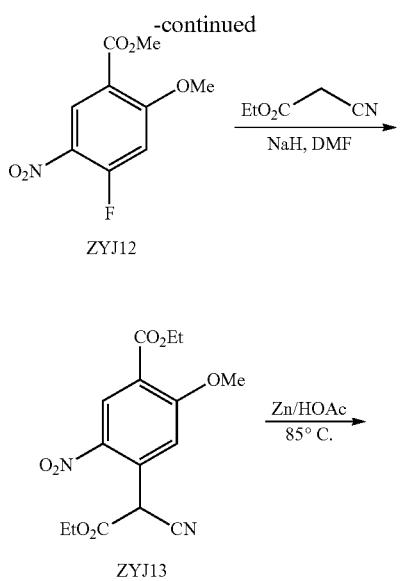
ZYJ12
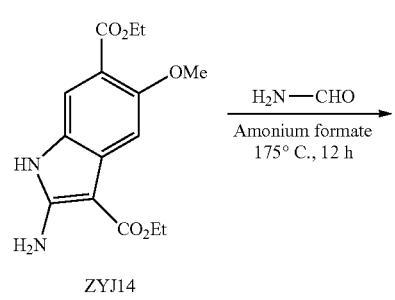
ZYJ13
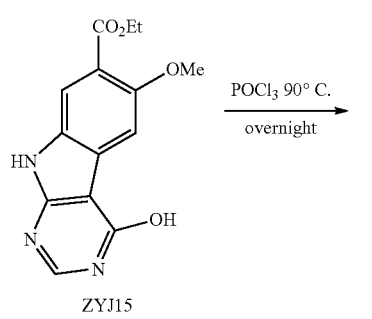
ZYJ14
ZYJ15
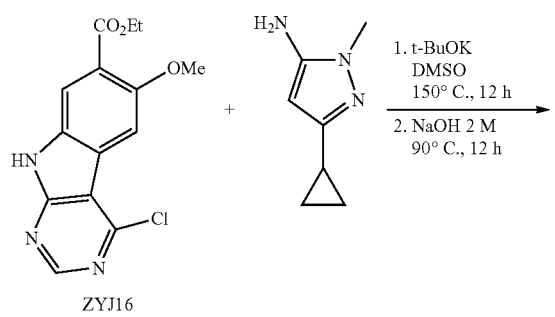
ZYJ16
-continued
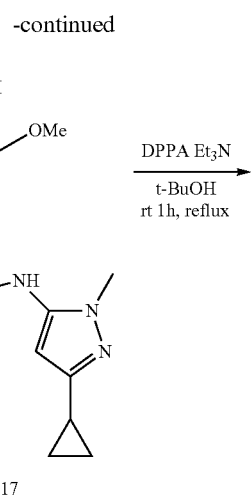
ZYJ17
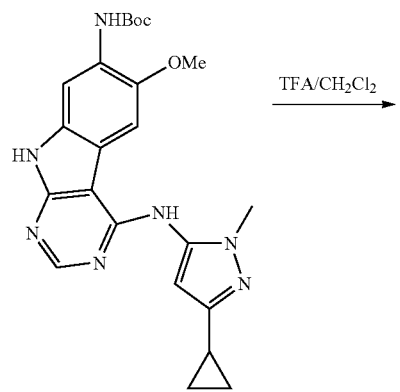
ZYJ18
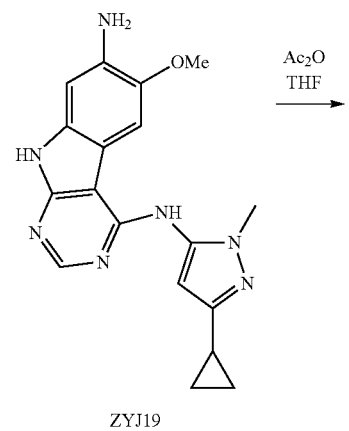
ZYJ19

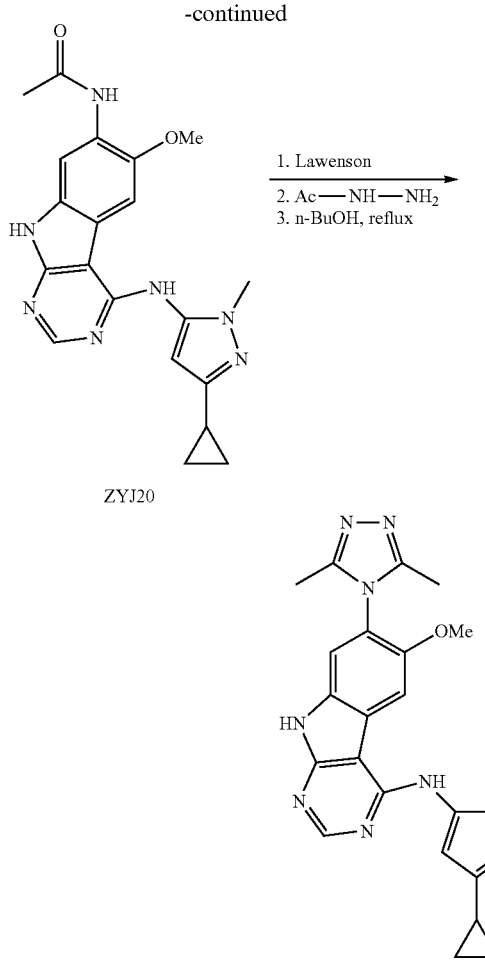

ZYJ20

Step 1: Methyl 4-fluoro-2-methoxybenzoate (7.07 g, 38.4 mmol) was dissolved in concentrated sulfuric acid (50 mL). The reaction mixture was cooled to 0° C. and KNO$_3$ (4.26 g, 42.2 mmol) was added in small portions. The reaction was stirred was warm up to ambient temperature and after 3 h, the mixture was poured into ice water. The solid was collected by filtration and dried on vacuum affording ZYJ12 (8.24 g) as a solid. $^1$H NMR (400 MHz, CDCl$_3$): 8.72 (d, J=8.79 Hz, 1H), 6.85 (d, J=12.69 Hz, 1H), 4.03 (s, 3H), 3.95 (s, 3H).

Step 2: NaH (3.6 g, 90 mmol, 60% in mineral oil) was placed in a dry round-bottom flask and anhydrous DMF (100 mL) was added. The reaction was cooled with ice-water bath and ethyl cyanoacetate (4.90 g, 43.2 mmol) was added via a syringe and the mixture was stirred for 30 min. ZYJ12 (8.24 g, 36 mmol) was added as a DMF solution and the mixture was stirred at ambient temperature for overnight. The reaction mixture was then poured into ice water and extracted with diethyl ether. The aqueous layer was acidified with 0.5 N HCl and extracted with ethyl acetate. The aqueous layer was extracted with ethyl acetate, the combined organic layers were washed with brine, then dried over anhydrous Na$_2$SO$_4$. The volatile components were removed on a rotary evaporator and the residues were purified by flash column chromatography to yield ZYJ13 as a liquid in 9.66 g (minor isomer as Ethyl ester). $^1$H NMR (400 MHz, CDCl$_3$): 8.76 (s, 1H), 7.33 (s, 1H), 5.83 (s, 1H), 4.43 (q, J=7.13 Hz, 2H), 4.34 (q, J=7.15 Hz, 2H), 4.10 (s, 3H), 1.43 (t, J=7.14 Hz, 3H), 1.36 (t, J=7.14 Hz, 3H).

Step 3: ZYJ13 (9.66 mmol, 28.7 mmol) was dissolved in acetic acid (100 mL) and the mixture was heated up at 85° C. Zinc powder (7.8 g, 120 mmol) was added in small portions and the reaction mixture was stirred at 85° C. for 1 h. Another 7.8 g of zinc powder was added again and the reaction mixture was heated at 85° C. for 12 h. The reaction was cooled to room temperature and filtered, washed with ethyl acetate. The organic layer was concentrated on a rotatory evaporator and re-dissolved in ethyl acetate. The solution was neutralized with saturated aqueous sodium bicarbonate solution. The aqueous layer was extracted with ethyl acetate, the combined organic layers were washed with brine, then dried over anhydrous Na$_2$SO$_4$. The volatile components were removed on a rotary evaporator and the residues were purified by flash column chromatography to yield ZYJ14 in 5.82 g (the minor isomer as ethyl ester). ESI-MS calculated for minor isomer $C_{14}H_{17}N_2O_5$ [M+H]$^+$=293.11; Observed: 293.42.

Step 4: ZYJ14 (5.82 g, 19 mmol) and) and ammonium formate (2.40 g, 40 mmol) were mixed in formamide (30 mL) and the mixture heated at 175° C. for overnight. The reaction mixture was cooled to room temperature and water was added. The solid was collected by filtration and dried over high vacuum for overnight. The product ZYJ15 was obtained in 2.3 g as a solid (minor isomer as Ethyl ester). $^1$H NMR (400 MHz, DMSO-d6): 12.24 (s, 1H), 8.02 (s, 1H), 7.77 (s, 1H), 7.57 (s, 1H), 3.97 (s, 3H), 3.87 (s, 3H).

Step 5: ZYJ15 (1 g) and POCl$_3$ (15 mL) were mixed in a dry round-bottom flask and the mixture was heated at 90° C. for overnight. Volatile components were removed on a rotatory evaporator and the mixture was the diluted with ethyl acetate and poured into saturated aqueous sodium bicarbonate. The solid was washed with water and dried over high vacuum for overnight affording the desired product ZYJ16 (1.3 g) (minor isomer as Ethyl ester). $^1$H NMR (400 MHz, DMSO-d6): 8.66 (s, 1H), 7.94 (s, 1H), 7.83 (s, 1H), 4.00 (s, 3H), 3.94 (s, 3H).

Step 6: ZYJ16 (1.3 g, 4.2 mmol), 3-cyclopropyl-1-methyl-1H-pyrazol-5-amine (1.03, 7.5 mmol), and t-BuOK (2.24 g, 20 mmol) were mixed in a dry round-bottom flask. Anhydrous DMSO (25 mL) was added via a syringe and the mixture was heated at 150° C. for 12 h. The mixture was diluted with 2N aqueous sodium hydroxide solution (20 mL) and heated at 100° C. for overnight. The reaction was quenched with 250 mL water and pH was adjusted to 4 using 2 N HCl. The solution was filtered through a pad of Celite® and the Celite® was washed with methanol. The liquid solution was concentrated on a rotatory evaporator and the residue was diluted with 100 mL water. The aqueous layer was extracted with THF/ethyl acetate (4:1), the combined organic layers were concentrated on a rotatory evaporator and the residues were purified by reverse phase HPLC to yield ZYJ17 in 250 mg as salt of CF$_3$CO$_2$H. $^1$H NMR (400 MHz, MeOD-d4): 8.46 (s, 1H), 8.00 (s, 1H), 7.65 (s, 1H), 6.20 (s, 1H), 3.99 (s, 3H), 3.79 (s, 3H), 2.02-1.92 (m, 1H), 1.02-0.97 (m, 2H), 0.84-0.76 (m, 2H). ESI-MS calculated for $C_{19}H_{19}N_6O_3$ [M+H]$^+$=379.15; Observed: 379.20.

Step 6: ZYJ17 (250 mg, 0.66 mmol) and triethylamine (0.5 mL, 3.6 mmol) was dissolved in anhydrous t-BuOH (10 mL). Diphenylphosphoryl azide (0.27 mL, 1.5 mmol) was added via a syringe and the mixture was stirred at ambient temperature for 1 h then heated at reflux for overnight. t-BuOH was removed on a rotatory evaporator and the remaining residues were purified by flash column chromatography to yield ZYJ18 in 240 mg. Subject ZYJ18 to CF$_3$CO$_2$H/CH$_2$Cl$_2$ (10 mL) and TES-H (0.2 mL) at room temperature for 4 h. The reaction mixture was concentrated on a rotatory evaporator and the remaining residues were purified by flash column chromatography to yield ZYJ19 in 50 mg. $^1$H NMR (300 MHz, DMSO-d6): 8.43 (s, 1H), 7.87 (s, 1H), 7.43 (s, 1H), 6.05 (s, 1H), 3.95 (s, 3H), 3.59 (s, 3H), 1.92-1.80 (m, 1H), 0.92-0.80 (m, 2H), 0.70-0.60 (m, 2H). ESI-MS calculated for $C_{18}H_{20}N_7O$ $[M+H]^+=350.17$; Observed: 350.58.

Step 7: ZYJ19 (50 mg, 0.15 mmol) was dissolved in anhydrous THF (5 mL). Acetic anhydride (0.04 mL, 0.4 mmol) was added via a syringe. The reaction was stirred at ambient temperature for 2 h. The reaction was concentrated on a rotatory evaporator and the remaining residues were purified by reverse phase HPLC to yield ZYJ20 in 40 mg. $^1$H NMR (300 MHz, MeOD-d4): 8.56 (s, 1H), 8.43 (s, 1H), 7.59 (s, 1H), 6.17 (s, 1H), 4.01 (s, 3H), 3.75 (s, 3H), 2.25 (s, 3H), 2.10-1.90 (m, 1H), 1.10-0.90 (m, 2H), 0.80-0.70 (m, 2H). ESI-MS calculated for $C_{20}H_{22}N_7O_2$ $[M+H]^+=392.18$; Observed: 392.2.

Step 8: ZYJ20 (20 mg) and Lawesson reagent (80 mg) were dissolved in anhydrous 1,4-dixoane and the reaction mixture was reflux for 6 h. The reaction mixture was concentrated on a rotatory evaporator and acethydrazide (50 mg) and n-BuOH were added. The reaction mixture was stirred at ambient temperature for 1 h then heated at 90° C. for overnight. The reaction was concentrated on a rotatory evaporator and the remaining residues were purified by reverse phase HPLC to yield the titled compound in 1.4 mg as a salt of $CF_3CO_2H$. $^1$H NMR (400 MHz, MeOD-d4): 8.45 (s, 1H), 7.94 (s, 1H), 7.76 (s, 1H), 6.03 (s, 1H), 3.99 (s, 3H), 3.72 (s, 3H), 2.42 (s, 6H), 2.00-1.90 (m, 1H), 1.00-0.90 (m, 2H), 0.80-0.70 (m, 2H). ESI-MS calculated for $C_{22}H_{24}N_9O$ $[M+H]^+=430.21$; Observed: 430.33.

Example 5

Synthesis of N-(3-Cyclopropyl-1-(pyridin-4-yl)-1H-pyrazol-5-yl)-7-(3,5-dimethylisoxazol-4-yl)-6-methoxy-2-methyl-9H-pyrimido[4,5-b]indol-4-amine (Cpd. No. 9)

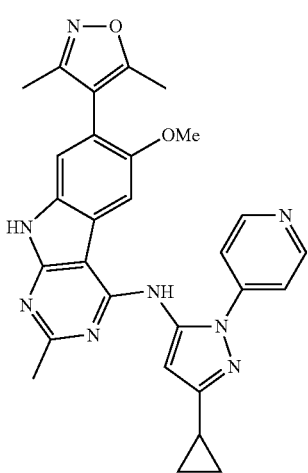 [SMILES: COc1cc2c(cc1-c1c(C)noc1C)[nH]c1nc(C)nc(Nc3cc(C4CC4)nn3-c3ccncc3)c12]

Step 1: Synthesis of 3-Cyclopropyl-1-(pyridin-4-yl)-1H-pyrazol-5-amine

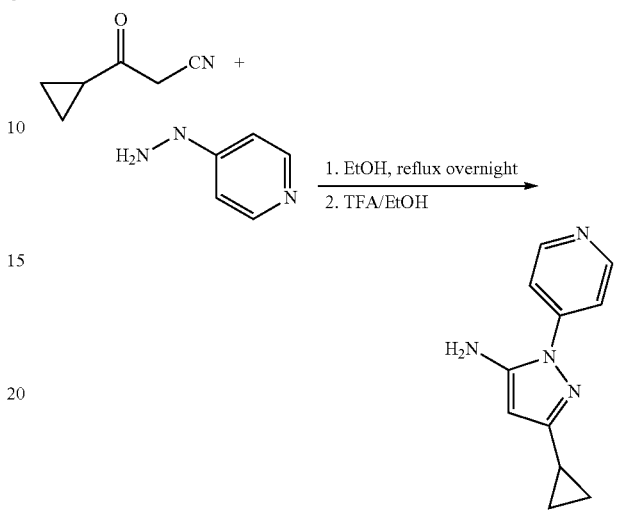

3-Cyclopropyl-3-oxopropanenitrile (3.30 g, 30 mmol) and 4-hydrazinylpyridine-HCl (3 g, 20 mmol) were dissolved in ethanol and the solution was heated at reflux for 12 h. The reaction mixture was concentrated and re-dissolved in ethyl acetate. The solution was neutralized with NaOH solution and the aqueous layer was extracted with ethyl acetate, the combined organic layers were washed with brine, then dried over anhydrous $Na_2SO_4$. The volatile components were removed on a rotary evaporator and the residues were dissolved in methanol (10 mL) followed by addition of $CF_3CO_2H$ (10 mL). The reaction mixture was stirred at room temperature for 12 h and the volatile components were removed on a rotary evaporator. The remaining residues were purified by flash column chromatography affording 3-cyclopropyl-1-(pyridin-4-yl)-1H-pyrazol-5-amine in 3.52 g. $^1$H NMR (300 MHz, MeOD-d4): 8.56 (dd, J=4.75, 1.58 Hz, 2H), 7.68 (dd, J=4.74, 1.59 Hz, 2H), 5.58 (s, 1H), 1.84-1.74 (m, 1H), 0.90-0.82 (m, 2H), 0.66-0.60 (m, 2H). ESI-MS calculated for C11H13N4 $[M+H]^+=201.11$; Observed: 201.58.

Step 2: Synthesis of N-(3-Cyclopropyl-1-(pyridin-4-yl)-1H-pyrazol-5-yl)-7-(3,5-dimethylisoxazol-4-yl)-6-methoxy-2-methyl-9H-pyrimido[4,5-b]indol-4-amine (Cpd. No. 9)

$Pd_2(dba)_3$ (46 mg) and racemic BINAP (62 mg) were mixed in anhydrous toluene (5 mL). The mixture was heated at reflux for 5 min and then it was cooled to ambient temperature. The solution was transferred into a second round-bottom flask containing 4-(4-chloro-6-methoxy-2-methyl-9H-pyrimido[4,5-b]indol-7-yl)-3,5-dimethylisoxazole (referred to herein as "S13") (170 mg, 0.5 mmol), 3-cyclopropyl-1-(pyridin-4-yl)-1H-pyrazol-5-amine (285 mg, 1 mmol), tert-BuONa (500 mg), and anhydrous toluene (8 mL). The mixture was degassed and heated at reflux for overnight before quenching with methanol at ambient temperature. The reaction mixture was filtered through a pad of celite, washed with methanol and the collected liquid solution was acidified with trifluoroacetic acid. The solution was then concentrated on a rotary evaporator and the remaining residues was purified by reverse phase HPLC to yield Cpd. No. 9 in 40 mg as a salt of $CF_3CO_2H$. $^1H$ NMR (400 MHz, MeOD-d4): 8.72 (d, J=6.48 Hz, 2H), 8.46 (d, J=6.53 Hz, 2H), 7.71 (s, 1H), 7.47 (s, 1H), 6.45 (s, 1H), 3.89 (s, 3H), 2.57 (s, 3H), 2.33 (s, 3H), 2.15 (s, 3H), 2.15-2.05 (m, 1H), 1.18-1.05 (m, 2H), 0.98-0.9 (m, 2H). ESI-MS calculated for $C_{28}H_{27}N_8O_2$ $[M+H]^+$=507.23; Observed: 507.25.

Example 6

Synthesis of 4-(3-Cyclopropyl-5-((7-(3,5-dimethyl-isoxazol-4-yl)-6-methoxy-2-methyl-9H-pyrimido[4,5-b] indol-4-yl)amino)-1H-pyrazol-1-yl)benzoic acid (Cpd. No. 10)

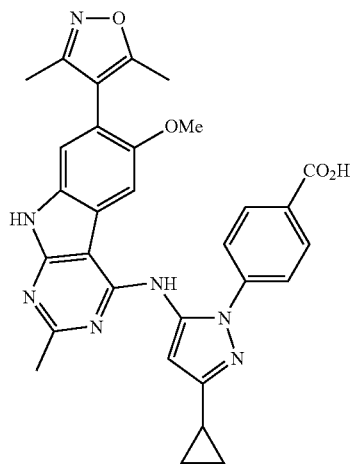 [SMILES: COc1cc2c(cc1-c1c(C)noc1C)[nH]c1nc(C)nc(Nc3cc(C4CC4)nn3-c3ccc(C(=O)O)cc3)c12]

Step 1: Synthesis of 4-(5-Amino-3-cyclopropyl-1H-pyrazol-1-yl)benzoic acid

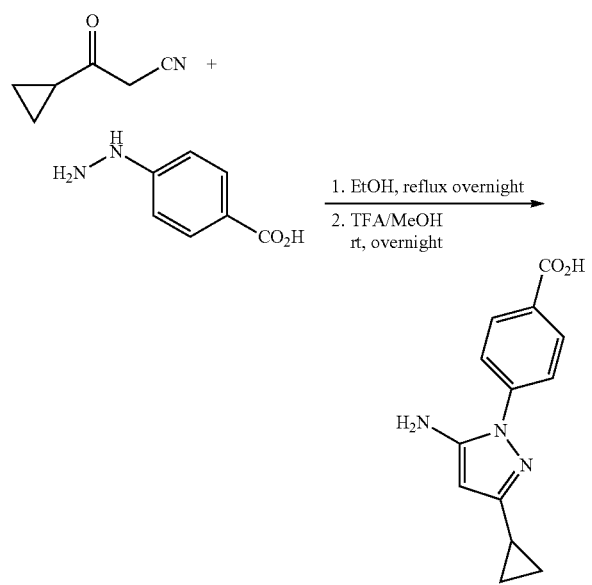

3-Cyclopropyl-3-oxopropanenitrile (2.61 g, 24 mmol) and 4-hydrazinylbenzoic acid (3.0 g, 20 mmol) were dissolved in ethanol and the solution was heated at reflux for 12 h. The reaction mixture was concentrated and re-dissolved in methanol (30 mL) followed by addition of $CF_3CO_2H$ (15 mL). The reaction mixture was stirred at room temperature for 12 h and the volatile components were removed on a rotary evaporator. The remaining residues were washed with ethyl acetate and 4-(5-amino-3-cyclopropyl-1H-pyrazol-1-yl)benzoic acid was collected by filtration as a solid (6.44 g). $^1H$ NMR (400 MHz, DMSO-d6): 8.02 (d, J=8.70 Hz, 2H), 7.74 (d, J=8.70 Hz, 2H), 5.30 (s, 1H), 1.85-1.75 (m, 1H), 0.95-0.85 (m, 2H), 0.73-0.65 (m, 2H). ESI-MS calculated for $C_{13}H_{14}N_3O_2$ $[M+H]^+$=244.11; Observed: 244.1.

Step 2: Synthesis of 4-(3-Cyclopropyl-5-((7-(3,5-dimethylisoxazol-4-yl)-6-methoxy-2-methyl-9H-pyrimido[4,5-b] indol-4-yl)amino)-1H-pyrazol-1-yl) benzoic acid (Cpd. No. 10)

Cpd. No. 10 was prepared from S13 (170 mg, 0.5 mmol) and 4-(5-amino-3-cyclopropyl-1H-pyrazol-1-yl)benzoic acid (250 mg, 1 mmol) following a similar procedure for the preparation of Cpd. No. 9. The titled compound was obtained in 50 mg as a salt of $CF_3CO_2H$. $^1H$ NMR (400 MHz, MeOD-d4): 7.97 (d, J=8.64 Hz, 2H), 7.64 (d, J=8.64 Hz, 2H), 7.44 (s, 1H), 7.28 (s, 1H), 6.40 (s, 1H), 3.83 (s, 3H), 2.62 (s, 3H), 2.31 (s, 3H), 2.14 (s, 3H), 2.10-2.00 (m, 1H), 1.10-1.00 (m, 2H), 0.88-0.80 (m, 2H). ESI-MS calculated for $C_{30}H_{28}N_7O_4$ $[M+H]^+$=550.22; Observed: 550.3.

Example 6

Synthesis of N-(3-Cyclopropyl-1'-methyl-1'H-[1,4'-bipyrazol]-5-yl)-7-(3,5-dimethylisoxazol-4-yl)-6-methoxy-2-methyl-9H-pyrimido[4,5-b]indol-4-amine (Cpd. No. 12)

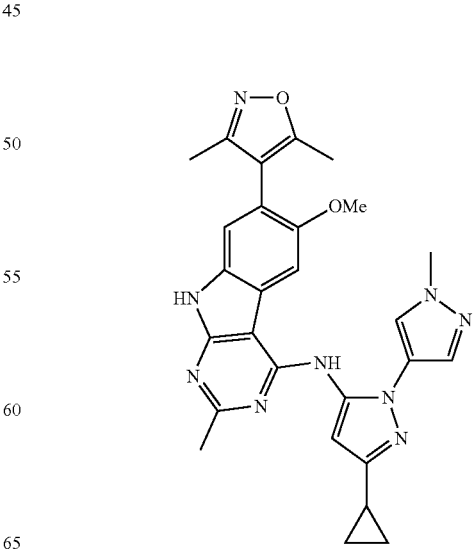

and N-(5-Cyclopropyl-1'-methyl-1'H-[1,4'-bipyrazol]-3-yl)-7-(3,5-dimethylisoxazol-4-yl)-6-methoxy-2-methyl-9H-pyrimido[4,5-b]indol-4-amine (Cpd. No. 13)

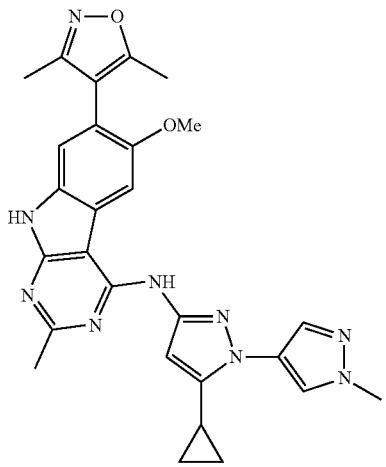

Step 1: Synthesis of 3-Cyclopropyl-1'-methyl-1'H-[1,4'-bipyrazol]-5-amine and 5-cyclopropyl-1'-methyl-1'H-[1,4'-bipyrazol]-3-amine

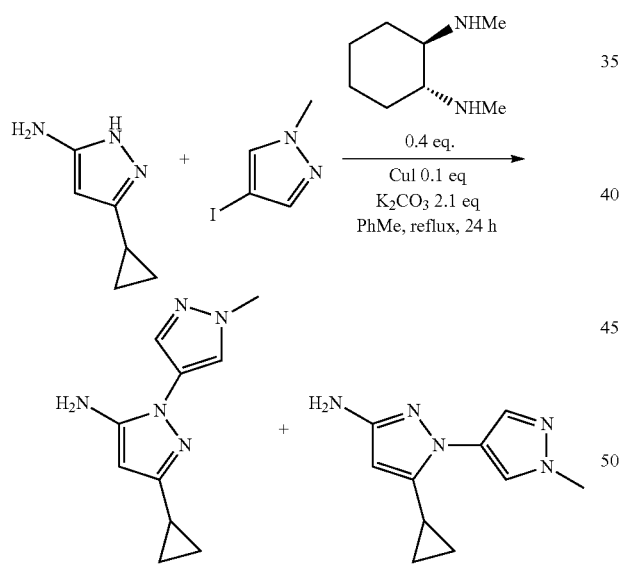

3-Cyclopropyl-1H-pyrazol-5-amine (615 mg, 5.0 mmol), 4-iodo-1-methyl-H-pyrazole (1.04 g, 5 mmol), potassium carbonate (1.5 g, 10.5 mmol) and CuI (95 mg, 0.50 mmol) were placed in a dry round-bottom flask. Anhydrous toluene was added via a syringe and the system was degassed. trans-N,N'-Dimethylcyclohexane-1,2-diamine (284 mg, 2.0 mmol) was added in one portion and the system was degassed followed by heating at reflux for 24 h. The reaction mixture was quenched with water. The aqueous layer was extracted with ethyl acetate, the combined organic layers were washed with brine, then dried over anhydrous $Na_2SO_4$. The volatile components were removed on a rotary evaporator and the residues were purified by flash column chromatography to yield the titled compound in 300 mg as a mixture of two isomers. $^1$H NMR (400 MHz, CDCl$_3$) major isomer: 7.66 (s, 1H), 7.63 (s, 1H), 5.24 (s, 1H), 3.92 (s, 3H), 3.80-3.70 (br, 2H), 1.90-1.80 (m, 1H), 0.92-0.82 (m, 2H), 0.74-0.66 (m, 2H). Minor isomer: 7.01 (s, 1H), 7.61 (s, 1H), 5.32 (s, 1H), 3.92 (s, 3H), 0.92-0.82 (m, 2H), 1.78-1.68 (m, 1H), 1.00-0.92 (m, 2H), 0.74-0.66 (m, 2H). Isomer ratio: 1.85:1.00 ESI-MS calculated for $C_{10}H_{14}N_5$[M+H]$^+$=204.12; Observed: 204.1.

Step 2: Synthesis of N-(3-Cyclopropyl-1'-methyl-1'H-[1,4'-bipyrazol]-5-yl)-7-(3,5-dimethylisoxazol-4-yl)-6-methoxy-2-methyl-9H-pyrimido[4,5-b]indol-4-amine (Cpd. No. 12) and N-(5-Cyclopropyl-1'-methyl-1'H-[1,4'-bipyrazol]-3-yl)-7-(3,5-dimethylisoxazol-4-yl)-6-methoxy-2-methyl-9H-pyrimido[4,5-b]indol-4-amine (Cpd. No. 13)

Cpd. Nos. 12 and 13 were prepared from S13 (342 mg, 0.5 mmol) and a mixture of 3-cyclopropyl-1'-methyl-1'H-[1,4'-bipyrazol]-5-amine and 5-cyclopropyl-1'-methyl-1'H-[1,4'-bipyrazol]-3-amine (300 mg) following a similar procedure for the preparation of Cpd. No. 9. Cpd. No. 12 was obtained as a minor product in 31.6 mg as a salt of $CF_3CO_2H$. $^1$H NMR (400 MHz, MeOD-d4): 7.91 (s, 1H), 7.65 (s, 1H), 7.47 (s, 1H), 7.14 (s, 1H), 6.31 (s, 1H), 3.86 (s, 3H), 3.84 (s, 3H), 2.72 (s, 3H), 2.33 (s, 3H), 2.15 (s, 3H), 2.06-1.96 (m, 1H), 1.08-0.98 (m, 2H), 0.84-0.78 (m, 2H). ESI-MS calculated for $C_{27}H_{28}N_9O_2$ [M+H]$^+$=510.24; Observed: 510.3. Cpd. No. 13 was obtained as a major product in 92 mg as a salt of $CF_3CO_2H$. $^1$H NMR (400 MHz, MeOD-d4): 8.20 (s, 1H), 8.10 (s, 1H), 7.86 (s, 1H), 7.45 (s, 1H), 6.22 (s, 1H), 4.01 (s, 3H), 3.93 (s, 3H), 2.77 (s, 3H), 2.32 (s, 3H), 2.15 (s, 3H), 2.00-1.88 (s, 1H), 1.20-1.10 (m, 2H), 0.88-0.78 (m, 2H). ESI-MS calculated for $C_{27}H_{28}N_9O_2$ [M+H]$^+$=510.24; Observed: 510.3.

Example 7

Synthesis of N-(3-Cyclopropyl-1-(1-methyl-1H-imidazol-4-yl)-1H-pyrazol-5-yl)-7-(3,5-dimethylisoxazol-4-yl)-6-methoxy-2-methyl-9H-pyrimido[4,5-b]indol-4-amine (Cpd. No. 14)

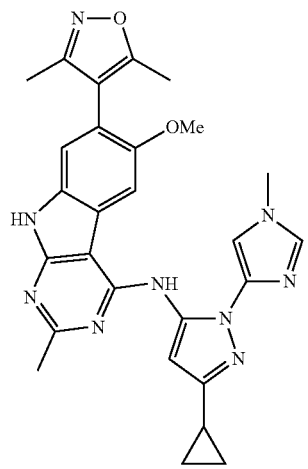 [SMILES: COc1cc2c(cc1-c1c(C)noc1C)[nH]c1nc(C)nc(Nc3cc(C4CC4)nn3-c3cn(C)cn3)c12]

Step 1: Synthesis of 3-Cyclopropyl-1-(1-methyl-1H-imidazol-4-yl)-1H-pyrazol-5-amine Example 8

Synthesis of N4-(3-cyclopropyl-1-isopropyl-1H-pyrazol-5-yl)-7-(3,5-dimethylisoxazol-4-yl)-6-methoxy-9H-pyrimido[4,5-b]indole-2,4-diamine (Cpd. No. 2)

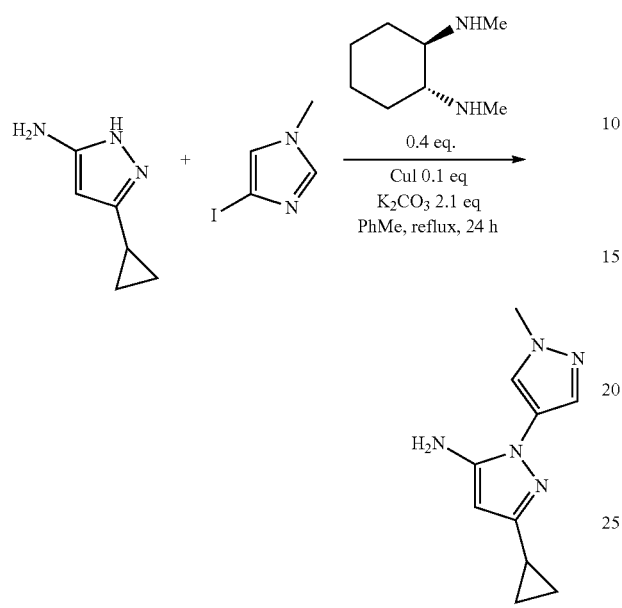

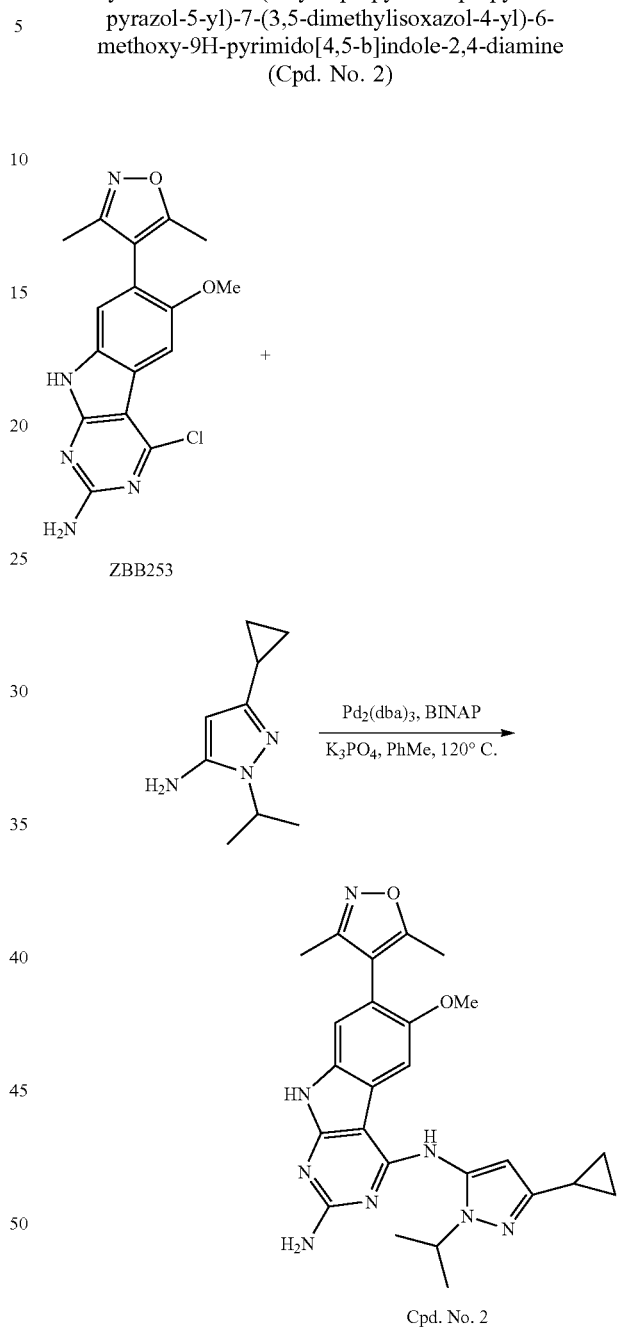

3-Cyclopropyl-1H-pyrazol-5-amine (910 mg, 7.4 mmol), 4-iodo-1-methyl-1H-imidazole (1.85 g, 8.9 mmol), potassium carbonate (2.2 g, 15.5 mmol) and CuI (140 mg, 0.74 mmol) were placed in a dry round-bottom flask. Anhydrous toluene was added via a syringe and the system was degassed. trans-N,N'-Dimethylcyclohexane-1,2-diamine (420 mg, 2.96 mmol) was added in one portion and the system was degassed followed by heating at reflux for 24 h. The reaction mixture was quenched with water. The aqueous layer was extracted with ethyl acetate, the combined organic layers were washed with brine, then dried over anhydrous $Na_2SO_4$. The volatile components were removed on a rotary evaporator and the residues were purified by flash column chromatography to yield the titled compound in 479 mg. $^1$H NMR (400 MHz, $CDCl_3$): 7.16 (s, 1H), 6.94 (s, 1H), 5.16 (br, 1H), 5.03 (s, 1H), 3.59 (s, 3H), 1.84-1.74 (m, 1H), 0.84-0.76 (m, 2H), 0.66-0.58 (m, 2H). ESI-MS calculated for $C_{10}H_{14}N_5$ $[M+H]^+$=204.12; Observed: 204.1.

Step 2: Synthesis of N-(3-Cyclopropyl-1-(1-methyl-1H-imidazol-4-yl)-1H-pyrazol-5-yl)-7-(3,5-dimethylisoxazol-4-yl)-6-methoxy-2-methyl-9H-pyrimido[4,5-b]indol-4-amine (Cpd. No. 14)

Cpd. No. 14 was prepared from S13 (342 mg, 0.5 mmol) and 3-cyclopropyl-1-(1-methyl-1H-imidazol-4-yl)-1H-pyrazol-5-amine (470 mg, 2.35 mmol) following a similar procedure for the preparation of Cpd. No. 9. The titled compound was obtained as a minor product in 60 mg as a salt of $CF_3CO_2H$. $^1$H NMR (400 MHz, MeOD-d4): 8.05 (s, 1H), 7.50 (s, 1H), 7.29 (s, 1H), 6.78 (s, 1H), 5.39 (s, 1H), 4.02 (s, 3H), 3.82 (s, 3H), 2.85 (s, 3H), 2.36 (s, 3H), 2.20 (s, 3H), 2.04-1.94 (m, 1H), 1.10-0.98 (m, 2H), 0.90-0.80 (m, 2H). ESI-MS calculated for $C_{27}H_{28}N_9O_2$ $[M+H]^+$=510.24; Observed: 510.3.

$Pd_2(dba)_3$ (18 mg) and BINAP (26 mg) were mixed in anhydrous toluene. And the mixture was heated at reflux for 3-4 minutes. This mixture was transferred into a round-bottom flask containing ZBB253 (60 mg), 3-cyclopropyl-1-isopropyl-1H-pyrazol-5-amine (84 mg), $K_3PO_4$ (130 mg), and toluene (2 mL). The mixture was heated at reflux for overnight before quenching with methanol. The reaction mixture was filtered and the mixture was purified by HPLC to yield Cpd. No. 2 as a $CF_3CO_2H$ salt in 36 mg. ESI-MS calculated for $C_{25}H_{29}N_8O_2$ $[M+H]^+$=473.24; Observed: 473.56.

Example 9

Synthesis of 7-(3,5-dimethylisoxazol-4-yl)-6-methoxy-N4-(2-methyl-2,4,5,6-tetrahydrocyclopenta[c]pyrazol-3-yl)-9H-pyrimido[4,5-b]indole-2,4-diamine (Cpd. No. 3)

Example 10

Synthesis of 7-(3,5-dimethylisoxazol-4-yl)-N4-(2-ethyl-2,4,5,6-tetrahydrocyclopenta[c]pyrazol-3-yl)-6-methoxy-9H-pyrimido[4,5-b]indole-2,4-diamine (Cpd. No. 4)

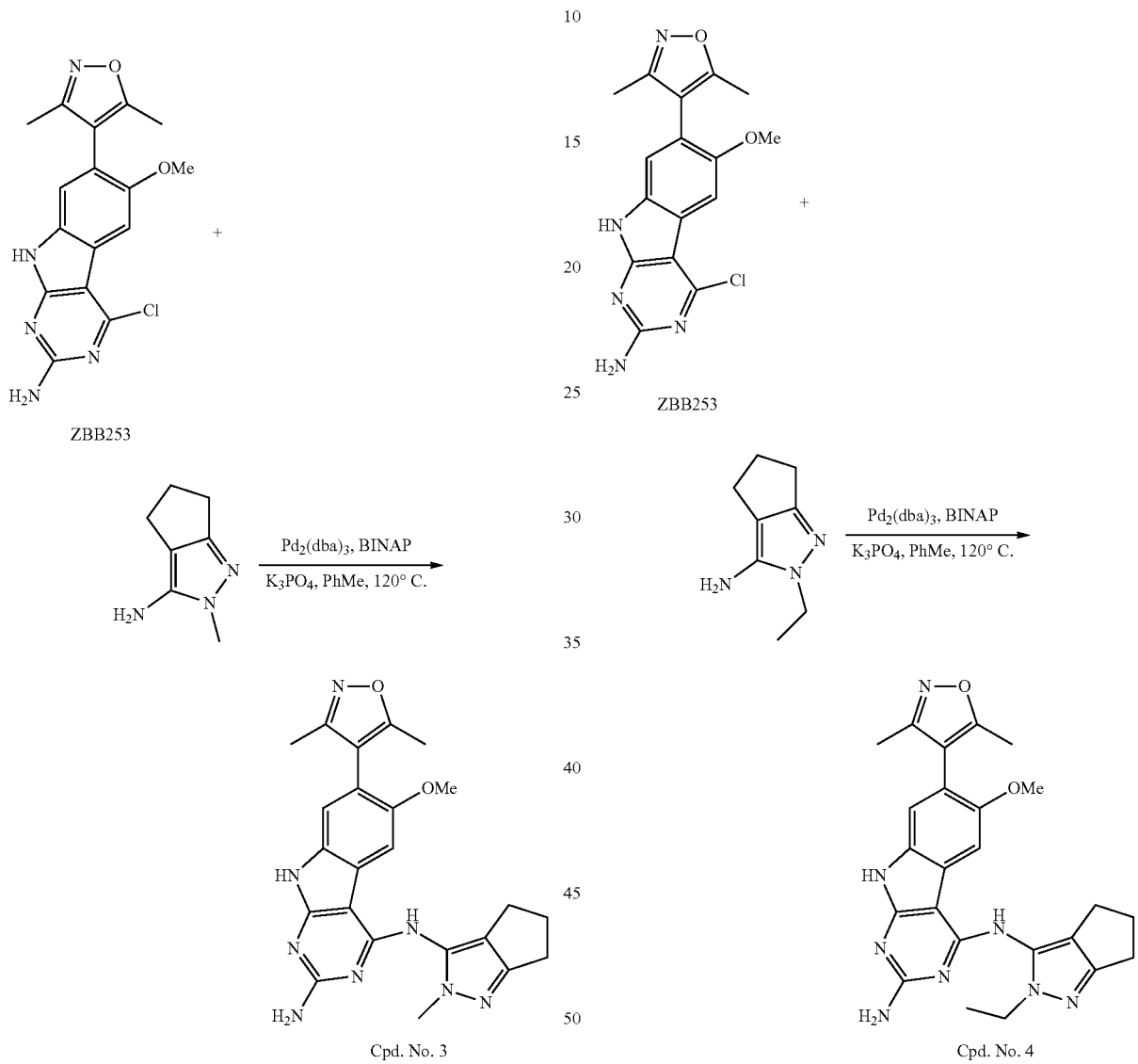

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB253 (60 mg), 2-methyl-2,4,5,6-tetrahydrocyclopenta[c]pyrazol-3-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 3 as a CF$_3$CO$_2$H salt in 33 mg. ESI-MS calculated for C$_{23}$H$_{25}$N$_8$O$_2$ [M+H]$^+$=445.21; Observed: 445.44.

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB253 (60 mg), 2-ethyl-2,4,5,6-tetrahydrocyclopenta[c]pyrazol-3-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 4 as a CF$_3$CO$_2$H salt in 39 mg. ESI-MS calculated for C$_{24}$H$_{27}$N$_8$O$_2$ [M+H]$^+$=459.22; Observed: 459.66.

Example 11

Synthesis of N-(3-cyclopropyl-1-ethyl-1H-pyrazol-5-yl)-7-(3,5-dimethylisoxazol-4-yl)-6-methoxy-2-(methoxymethyl)-9H-pyrimido[4,5-b]indol-4-amine (Cpd. No. 5)

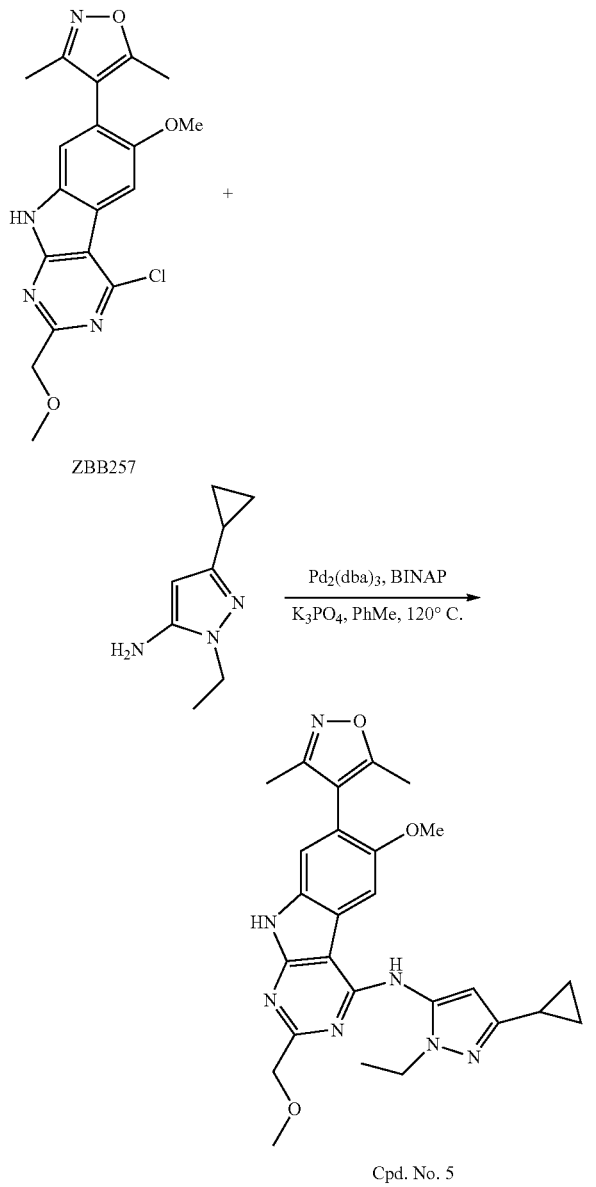 [SMILES: COCc1nc(Cl)c2c(n1)[nH]c1cc(-c3c(C)noc3C)c(OC)cc12 ; CCn1nc(C2CC2)cc1N ; CCn1nc(C2CC2)cc1Nc1nc(COC)nc2[nH]c3cc(-c4c(C)noc4C)c(OC)cc3c12]

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB257 (60 mg), 3-cyclopropyl-1-ethyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 5 as a CF$_3$CO$_2$H salt in 39 mg. ESI-MS calculated for C$_{26}$H$_{30}$N$_7$O$_3$ [M+H]$^+$=488.24; Observed: 488.44. $^1$H NMR (400 MHz, MeOD) δ 7.46 (s, 1H), 7.15 (s, 1H), 6.00 (s, 1H), 4.66 (s, 2H), 4.12 (q, J=7.2 Hz, 2H), 3.87 (s, 3H), 3.57 (s, 3H), 2.32 (s, 3H), 2.15 (s, 3H), 2.04-1.88 (m, 1H), 1.44 (t, J=7.2 Hz, 3H), 1.03-0.91 (m, 2H), 0.78-0.64 (m, 2H). $^{13}$C (100 M Hz, MeOD-d4): 166.28, 159.70, 158.95, 154.72, 154.47, 154.40, 153.57, 152.68, 136.56, 131.60, 119.55, 118.62, 144.40, 113.44, 104.01, 98.51, 96.69, 72.35, 58.26, 55.36, 42.76, 13.98, 10.06, 9.22, 8.84, 7.10.

Example 12

Synthesis of 7-(3,5-dimethylisoxazol-4-yl)-N-(2-isopropyl-2,4,5,6-tetrahydrocyclopenta[c]pyrazol-3-yl)-6-methoxy-2-(methoxymethyl)-9H-pyrimido[4,5-b]indol-4-amine (Cpd. No. 6)

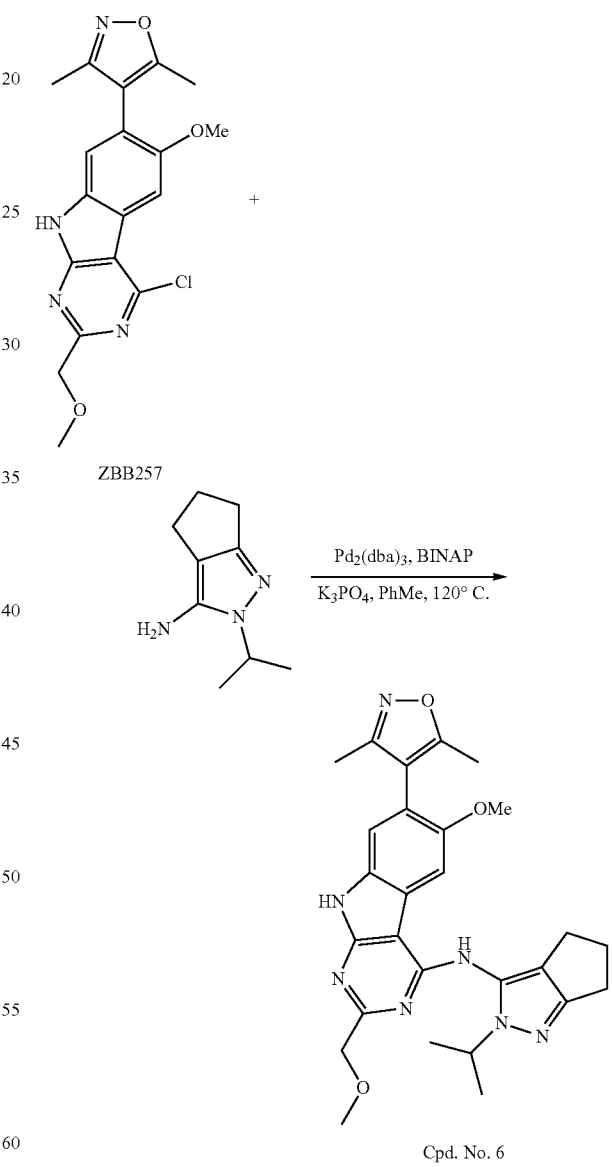

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB257 (60 mg), 2-isopropyl-2,4,5,6-tetrahydrocyclopenta[c]pyrazol-3-amine (84 mg), K₃PO₄ (130 mg), and toluene (2 mL). The mixture was heated at reflux for overnight before quenching with methanol. The reaction mixture was filtered and the mixture was purified by HPLC to yield Cpd. No. 6 as a CF₃CO₂H salt in 33 mg. ESI-MS calculated for $C_{27}H_{32}N_7O_3$ [M+H]⁺=502.25; Observed: 502.44.

Example 13

Synthesis of N-(3-cyclopropyl-1-isopropyl-1H-pyrazol-5-yl)-7-(3,5-dimethylisoxazol-4-yl)-6-methoxy-2-(methoxymethyl)-9H-pyrimido[4,5-b]indol-4-amine (Cpd. No. 7)

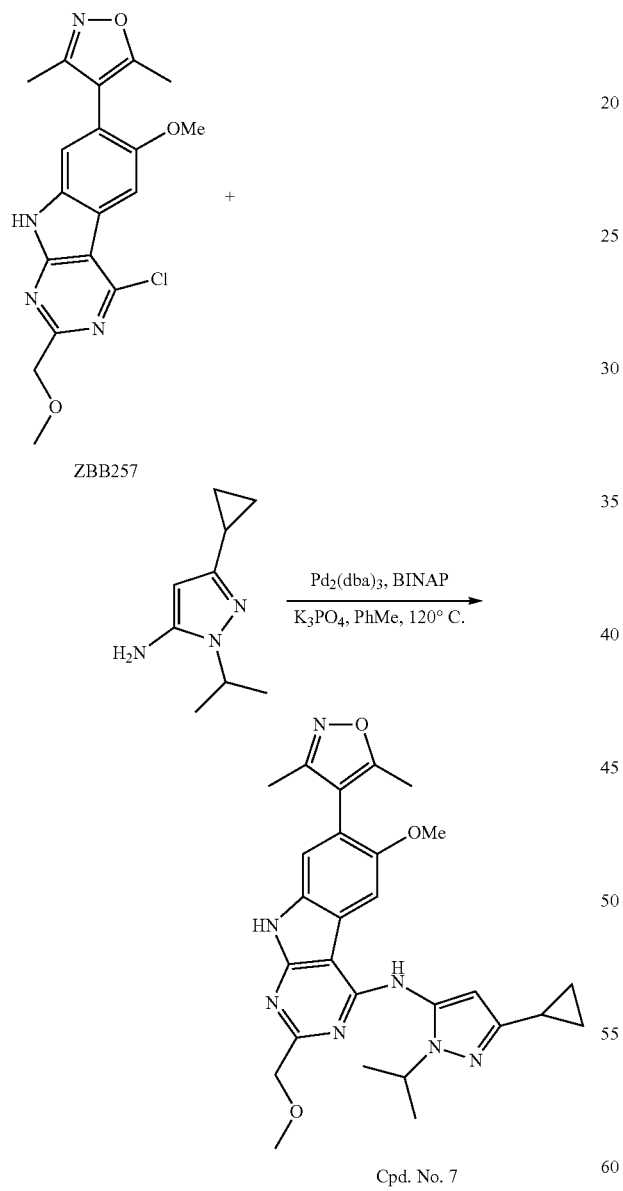

Pd₂(dba)₃ (18 mg) and BINAP (26 mg) were mixed in anhydrous toluene. And the mixture was heated at reflux for 3-4 minutes. This mixture was transferred into a round-bottom flask containing ZBB257 (60 mg), 3-cyclopropyl-1-isopropyl-1H-pyrazol-5-amine (84 mg), K₃PO₄ (130 mg), and toluene (2 mL). The mixture was heated at reflux for overnight before quenching with methanol. The reaction mixture was filtered and the mixture was purified by HPLC to yield Cpd. No. 7 as a CF₃CO₂H salt in 33 mg. ESI-MS calculated for $C_{27}H_{32}N_7O_3$ [M+H]⁺=502.25; Observed: 502.54. ¹H NMR (400 MHz, MeOD) δ 7.51 (s, 1H), 7.01 (s, 1H), 6.01 (s, 1H), 4.70 (s, 2H), 4.67-4.56 (m, 1H), 3.86 (s, 3H), 3.60 (s, 3H), 2.29 (s, 3H), 2.11 (s, 3H), 2.06-1.93 (m, 1H), 1.50 (d, J=6.7 Hz, 6H), 1.05-0.93 (m, 2H), 0.78-0.62 (m, 2H).

Example 14

Synthesis of N-(3-cyclopropyl-1-methyl-1H-pyrazol-5-yl)-7-(3,5-dimethyl-4H-1,2,4-triazol-4-yl)-6-methoxy-2-methyl-9H-pyrimido[4,5-b]indol-4-amine (Cpd. No. 15)

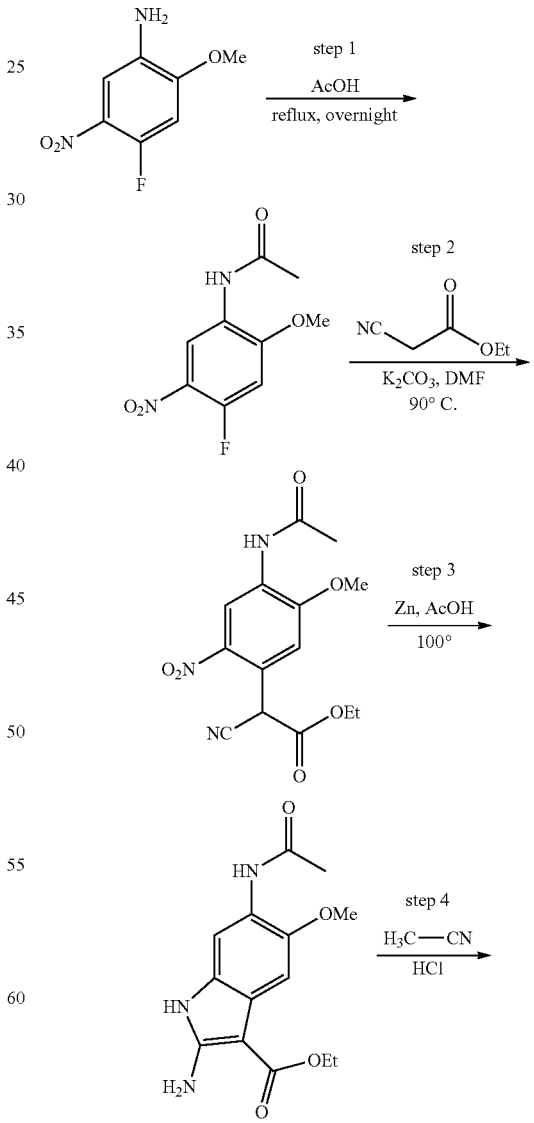

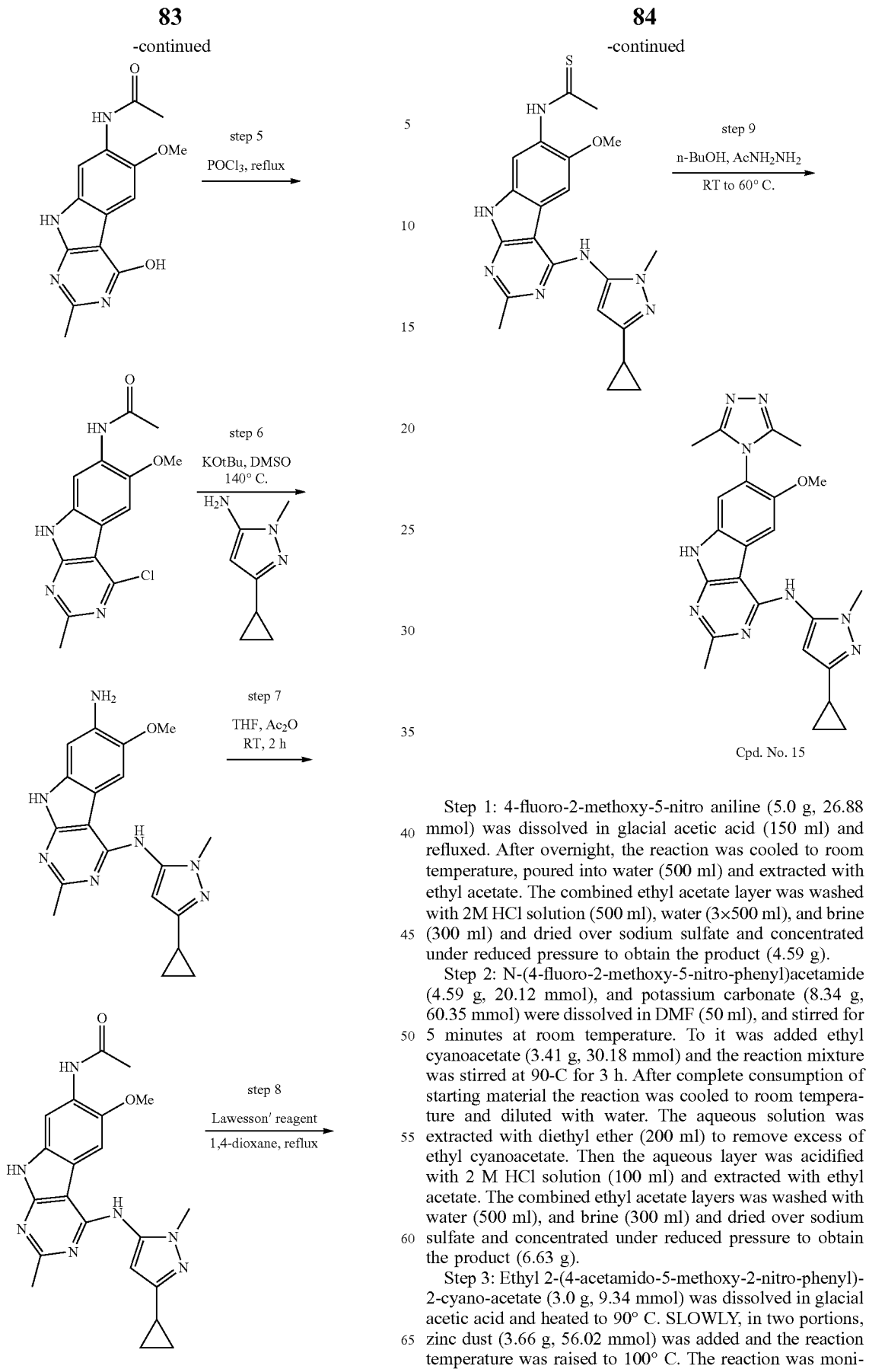

Step 1: 4-fluoro-2-methoxy-5-nitro aniline (5.0 g, 26.88 mmol) was dissolved in glacial acetic acid (150 ml) and refluxed. After overnight, the reaction was cooled to room temperature, poured into water (500 ml) and extracted with ethyl acetate. The combined ethyl acetate layer was washed with 2M HCl solution (500 ml), water (3×500 ml), and brine (300 ml) and dried over sodium sulfate and concentrated under reduced pressure to obtain the product (4.59 g).

Step 2: N-(4-fluoro-2-methoxy-5-nitro-phenyl)acetamide (4.59 g, 20.12 mmol), and potassium carbonate (8.34 g, 60.35 mmol) were dissolved in DMF (50 ml), and stirred for 5 minutes at room temperature. To it was added ethyl cyanoacetate (3.41 g, 30.18 mmol) and the reaction mixture was stirred at 90-C for 3 h. After complete consumption of starting material the reaction was cooled to room temperature and diluted with water. The aqueous solution was extracted with diethyl ether (200 ml) to remove excess of ethyl cyanoacetate. Then the aqueous layer was acidified with 2 M HCl solution (100 ml) and extracted with ethyl acetate. The combined ethyl acetate layers was washed with water (500 ml), and brine (300 ml) and dried over sodium sulfate and concentrated under reduced pressure to obtain the product (6.63 g).

Step 3: Ethyl 2-(4-acetamido-5-methoxy-2-nitro-phenyl)-2-cyano-acetate (3.0 g, 9.34 mmol) was dissolved in glacial acetic acid and heated to 90° C. SLOWLY, in two portions, zinc dust (3.66 g, 56.02 mmol) was added and the reaction temperature was raised to 100° C. The reaction was monitored with UPLC (if oxime byproduct is present, more zinc dust was added and reaction was heated until the byproduct was consumed). The reaction mass was filtered through Celite© in hot condition, washed with ethyl acetate (100 ml) and the filterate was diluted with water (500 ml) and again filtered through a small bed of Celite© again. The ethyl acetate layer was collected and the aqueous layer was again extracted with ethyl acetate (2×). The combined ethyl acetate layers was again washed with saturated sodium carbonate solution, brine and concentrated under reduced pressure to obtain the product (1.5 g).

Step 4: Ethyl 2-(4-acetamido-2-amino-5-methoxy-phenyl)-2-cyano-acetate (2.0 g, 8.67 mmol) was dissolved in acetonitrile (50 ml) and the solution was cooled to 0° C. At 0° C., dry HCl gas was bubbled through the solution for 30 minutes, then the reaction mass was refluxed for 2.5 h. After cooling to room temperature the reaction was concentrated to get the thick product, that was dissolved in ethanol (30 ml) and 10% NaOH (20 ml) solution and the resulting mixture was refluxed for 3 h. The reaction was then cooled to room temperature, concentrated under reduced pressure to remove ethanol. The resulting alkaline solution was diluted with water and acidified with 2M HCl solution and cooled at 5° C. The solid product obtained was filtered and dried to get the product (878 mg).

Step 5: N-(4-hydroxy-6-methoxy-2-methyl-9H-pyrimido[4,5-b]indol-7-yl)acetamide (488 mg, 1.71 mmol) was dissolved in POCl$_3$ (15 mL) and refluxed overnight. After cooling to room temperature the reaction was concentrated. The concentrate was slowly quenched with saturated sodium bicarbonate solution and extracted with ethyl acetate. The combined ethyl acetate layers was washed with brine, dried over sodium sulfate and concentrated under reduce pressure the give the product (384 mg).

Step 6: N-(4-chloro-6-methoxy-2-methyl-9H-pyrimido[4,5-b]indol-7-yl)acetamide (384 mg, 1.26 mmol), 3-cyclopropyl-1-methyl-1H-pyrazol-5-amine (520 mg, 3.79 mmol), and potassium tert-butoxide (709 mg, 6.32 mmol) were dissolved in DMSO (18 mL) and the reaction was heated to 140° C. After overnight the reaction was cooled to room temperature, quenched with saturated ammonium chloride, and extracted with ethyl acetate. The ethyl acetate layers was washed with brine, dried over sodium sulfate, concentrated under reduce pressure and purified by reverse phase preparative HPLC to give the product (58 mg).

Step 7: Acetic anhydride (65 mg, 0.637 mmol) was added to a solution of N$^4$-(3-cyclopropyl-1-methyl-1H-pyrazol-5-yl)-6-methoxy-2-methyl-9H-pyrimido[4,5-b]indole-4,7-diamine (58 mg, 0.159 mmol) dissolved in THF (3 mL). After 2 hours, the reaction was concentrated and columned to give the product (32 mg).

Step 8 and 9: Lawesson's reagent (31.3 mg, 0.0775 mmol) was added to a solution of N-(4-((3-cyclopropyl-1-methyl-1H-pyrazol-5-yl)amino)-6-methoxy-2-methyl-9H-pyrimido[4,5-b]indol-7-yl)acetamide (15.7 mg, 0.0387 mmol) dissolved in dry dioxane (3 mL) and the reaction was refluxed for six hours. After cooling to room temperature the reaction was concentrated in vacuo to yield the crude thioacetamide that was used without purification in the next step. Acetylhydrazide (14 mg, 0.194 mmol) was added to a solution of the crude thioacetamide dissolved in the n-butanol (2 mL) and the reaction was heated to 60° C. After overnight the reaction was cooled, n-butanol was removed under reduced pressure and the crude reaction was purified by reverse phase preparative HPLC to give the product Cpd. No. 15 (5 mg). $^1$H-NMR (400 MHz, CD$_3$OD) δ ppm 7.72 (s, 1H), 7.67 (s, 1H), 6.01 (s, 1H), 3.94 (s, 3H), 3.72 (s, 3H), 2.62 (s, 3H), 2.83 (s, 6H), 1.98-1.88 (m, 1H), 1.00-0.92 (m, 2H), 0.76-0.69 (m, 2H).

Example 15

Competitive Fluorescence-Polarization (FP) Assays

Fluorescence Polarization (FP) competitive binding studies were carried out using a FAM labeled fluorescent probe (ZBA248 or BRD-1F) to determine binding affinities of representative Compounds of the Disclosure for recombinant BRD4 BD1 and BRD4 BD2 proteins. For example, equilibrium dissociation constants ($K_d$) values of ZBA248 to these six proteins were determined from protein saturation experiments by monitoring the total fluorescence polarization of mixtures composed with the fluorescent probe at a fixed concentration and proteins with increasing concentrations up to full saturation. Serial dilutions of testing protein were mixed with ZBA248 to a final volume of 200 μl in the assay buffer. In order to achieve large dynamic rages, particularly for BD1 bromodomains, 100 mM phosphate buffer (pH=6.5, 0.01% Triton X-100 (Sigma, 282103) being added right before assays) was used as the assay buffer. Final ZBA248 concentration was 1.5 nM for all proteins. Plates were incubated at room temperature for 30 minutes with gentle shaking to assure equilibrium. FP values in millipolarization units (mP) were measured using the Infinite M-1000 plate reader (Tecan U.S., Research Triangle Park, N.C.) in Microfluor 1 96-well, black, round-bottom plates (Thermo Scientific, Waltham, Mass.) at an excitation wavelength of 485 nm and an emission wavelength of 530 nm. $K_d$ values of ZBA248 were calculated by fitting the sigmoidal dose-dependent FP increases as a function of protein concentrations using Graphpad Prism 6.0 software (Graphpad Software, San Diego, Calif.).

The IC$_{50}$ and K$_i$ values of representative Compounds of the Disclosure were determined in a competitive binding experiment as described above. Mixtures of 10 μl of the tested compounds in assay buffer with 40% Ethylene Glycol and 190 μl of preincubated protein/probe complex solution in the assay buffer (100 mM potassium phosphate, pH 6.5, 0.01% Triton X-100) were added into assay plates which were incubated at room temperature for 30 minutes with gentle shaking. Final concentrations of proteins were 10 and 6 nM in assays for BD1 and BD2 of BRD4, respectively. Final probe concentration is 1.5 nM in all assays. Negative controls containing protein/probe complex only (equivalent to 0% inhibition), and positive controls containing only free probes (equivalent to 100% inhibition), were included in each assay plate. FP values were measured as described above. IC$_{50}$ values were determined by nonlinear regression fitting of the competition curves. Instead of being calculated from IC$_{50}$ values as described before, K$_i$ values of competitive inhibitors were obtained directly by nonlinear regression fitting as well, based upon the $K_d$ values of the probe to different proteins, and concentrations of the proteins and probes in the competitive assays (Wang, *FEBS Lett.* 360; 111 (1995); Zhang et al., *Analytical Biochemistry,* 331; 138 (2004)).

Binding affinities of representative Compounds of the Disclosure to BRD4 BD1 and BRD4 BD2 proteins in competitive, fluorescence-polarization assays are presented in Table 2.

TABLE 2

| Cpd. No. | IC$_{50}$ (nM) | |
|---|---|---|
| | BRD4 BD1 | BRD4 BD2 |
| 1 | >1000 | >1000 |
| 2 | 1.0 | 2.1 |
| 3 | 3.5 | 1.6 |
| 4 | 1.0 | 2.5 |
| 5 | 5.5 | 2.4 |
| 6 | 3.6 | 2.9 |
| 7 | 3.9 | 2.1 |
| 8 | 652 | 1302 |
| 9 | 22.6 | 19.0 |
| 10 | 54.0 | 75.2 |
| 11 | 103 | 91.5 |
| 12 | 18.2 | 12.1 |
| 13 | 59.7 | 34.3 |
| 14 | 141 | 19.7 |
| 15 | 131 | 132 |
| 21 | >1000 | >1000 |

Binding affinities to BRD2 BD1 and BD2, BRD3 BD1 and BD2, and BRD4 BD1 and BD2 can also be determined by a label free binding assay using the OctetRED label free biolayer interferometry (BLI) binding assay.

Example 16

Cell Growth Inhibition

The effect of representative Compounds of the Disclosure on cell viability was determined in a 4-day proliferation assay. Cells were maintained in the appropriate culture medium with 10% FBS at 37° C. and an atmosphere of 5% CO2. All the cell lines were used within three months of thawing fresh vials.

Cells were seeded in 96-well flat bottom (Corning COSTAR, Corning, NY, cat#3595) or white opaque cell culture plates (BD Falcon, cat#353296) at a density of 3,000-10,000 cells/well in 75 μl of culture medium. Compounds were serially diluted in the appropriate medium, and 75 μl of the diluted compounds were added to the appropriate wells of the cell plate. After the addition of compounds, the cells were incubated at 37° C. in an atmosphere of 5% CO2 for 4 days. Cell viability was determined using the CellTiter-Glo® Luminescent Cell Viability Assay Kit (Promega, Madison, Wis.) for RS4-11 and MV4-11 cells and WST (2-(2-methoxy-4-nitrophenyl)-3-(4-nitrophenyl)-5-(2,4-disulfophenyl)-2H-tetrazolium, monosodium salt) Cell Counting-8 Kit (Dojindo Molecular Technologies, Inc., Rockville, Md.) for MDA-MB-231 cells according to the manufacturers' instructions.

For WST assay (MDA-MB-231 cells), WST-8 reagent was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The readings were normalized to the DMSO-treated cells and the half maximal inhibitory concentration (IC50) was calculated by nonlinear regression (four parameters sigmoid fitted with variable slope, least squares fit, and no constraint) analysis using the GraphPad Prism 5 software (GraphPad Software, La Jolla, Calif.).

For CellTiter-Glo assay (RS4-11 and MV4-11 cells), 100 μl of CellTiter-Glo® Reagent was added to each well, and then the plates were incubated at room temperature for 10-20 minutes. The luminescent signal was measured using a Tecan Infinite M1000 multimode microplate reader (Tecan, Morrisville, N.C.). The readings were normalized to the DMSO-treated cells and the IC50 was calculated by nonlinear regression (four parameters sigmoid fitted with variable slope, least squares fit, and no constraint) analysis using the GraphPad Prism 5 software.

Cell growth inhibition of representative Compounds of the Disclosure in representative breast cancer (MDA-MB-231), acute leukemia (MV4-11), and prostate cancer cell lines (LNCaP), as determined by a WST assay, are presented in Table 3. Cells were treated with each inhibitor for 4 days.

TABLE 3

| | IC$_{50}$ (μM) | | |
|---|---|---|---|
| Cpd. No. | MDA-MB-231 Cell Line | MV4-11 Cell Line | LNCaP Cell line |
| 2 | 0.046 | | 0.003 |
| 3 | 0.018 | | 0.067 |
| 4 | 0.006 | | 0.020 |
| 5 | 0.013 | 0.003 | 0.003 |
| 6 | 0.006 | 0.004 | |
| 7 | 0.006 | 0.003 | |
| 8 | >1 | | |
| 9 | 0.066 | | |
| 15 | 1.4 | | |

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof. All patents, patent applications and publications cited herein are fully incorporated by reference herein in their entirety.

What is claimed is:

1. A compound of Formula IV:

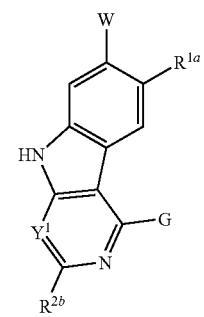

or a pharmaceutically acceptable salt, hydrate, or solvate thereof, wherein G is optionally substituted heteroaryl;
Y$^1$ is selected from the group consisting of —C(R$^{2a}$)═ and —N═;
R$^{1a}$ is selected from the group consisting of hydrogen, hydroxy, alkyl, haloalkyl, alkoxy, alkylthio, amino, and fluoro;
R$^{2b}$ is selected from the group consisting of hydrogen, halo, alkyl and carboxamido;
W is L; and
L is a leaving group.

2. The compound of claim 1, wherein G is optionally substituted 6-membered heteroaryl, or a pharmaceutically acceptable salt, hydrate, or solvate thereof.

3. The compound of claim 1, wherein $R^{1a}$ is —$OCH_3$, or a pharmaceutically acceptable salt, hydrate, or solvate thereof.

4. The compound of claim 1, wherein $Y^1$ is —N=, or a pharmaceutically acceptable salt, hydrate, or solvate thereof.

5. The compound of claim 1, wherein $Y^1$ is —CH=, or a pharmaceutically acceptable salt, hydrate, or solvate thereof.

6. The compound of claim 1, wherein L is selected from the group consisting of —Cl, —I, —Br, and —$OSO_2R^6$, wherein $R^6$ is selected from the group consisting of alkyl, haloalkyl, and optionally substituted aryl, or a pharmaceutically acceptable salt, hydrate, or solvate thereof.

* * * * *